US007892784B2

(12) United States Patent
Takagi et al.

(10) Patent No.: US 7,892,784 B2
(45) Date of Patent: Feb. 22, 2011

(54) LACTAM RING-OPENING ENZYME AND USE THEREOF

(75) Inventors: Hiroshi Takagi, Kyoto (JP); Yoshimitsu Hamano, Fukui (JP)

(73) Assignee: Fukui Prefectural University, Fukui (JP)

( * ) Notice: Subject to any disclaimer, the term of this patent is extended or adjusted under 35 U.S.C. 154(b) by 782 days.

(21) Appl. No.: 11/710,612

(22) Filed: Feb. 26, 2007

(65) Prior Publication Data

US 2007/0203075 A1 Aug. 30, 2007

(30) Foreign Application Priority Data

Feb. 27, 2006 (JP) ............................ 2006-050371

(51) Int. Cl.
*C12P 1/00* (2006.01)
*C12P 17/00* (2006.01)
*C12P 17/16* (2006.01)
*C12P 15/00* (2006.01)

(52) U.S. Cl. ........................ 435/41; 435/117; 435/118; 435/128

(58) Field of Classification Search ....................... None
See application file for complete search history.

(56) References Cited

PUBLICATIONS

Hamano et al. (A novel enzyme conferring streptothricin resistance alters the toxicity of streptothricin D from broad-spectrum to bacteria-specific, J Biol Chem., Jun. 23, 2006 281(25):16842-8, Epub Apr. 26, 2006).*

Branden et al., "Introduction to Protein Structure Second Edition", Garland Publishing Inc., New York, 1999.*

Witkowski et al., Biochemistry, 38, 11643-11650, 1999.*

Wishart et al., Journal of Biological Chemistry, vol. 270, No. 45, pp. 26782-26785, 1995.*

Kisselev, Structure, vol. 10, pp. 8-9, 2002.*

Waksman, "Production and Activity of Streptothricin" J. Bacteriol, vol. 46, pp. 299-310, 1943.

Partridge et al., "Correctly Identifying the Streptothricin Resistance Gene Cassette" J. Clin. Microciol. vol. 43, No. 8, pp. 4298-4300, Aug. 2005.

Singh et al., "Identification of antimicrobial resistance and class 1 integrons in Shiga toxin-producing *Escherichia coil* recovered from humans and food animals" J. Antimicrob. Chemother. vol. 56, pp. 216-219, May 2005.

Peirano et al., "Occurrence of integrons and resistance genes among sulphonamide-resistant Shigella spp. from Brazil" J. Antimicrob. Chemother. vol. 55, pp. 301-305, Jan. 2005.

Vakulenko et al., "Versatility of Aminoglycosides and Prospects for Their Future" Clinical Microbiology Reviews, vol. 16, No. 3, pp. 430-450, Jul. 2003.

Horinouchi et al., "Nucleotide Sequence of the Streptothricin Acetyltransferase Gene from Streptomyces lavendulae and Its Expression in Heterologous Hosts" Journal of Bacteriology, vol. 169, No. 5, pp. 1929-1937, May 1987.

Fernandez-Moreno et al., "Streptothricin Biosynthesis is Catalyzed by Enzymes Related to Nonribosomal Peptide Bond Formation" Journal of Bacteriology, vol. 179, No. 22, pp. 6929-6936, Nov. 1997.

Krugel et al., "Analysis of the nourseothricin-resistance gene (nat) of Streptomyces noursei" Gene, vol. 62, pp. 209-217, 1988.

Grammel et al., "A B-lysine adenylating enzyme and a B-lysine binding protein involved in poly B-lysine chain assembly in nourseothricin synthesis in Streptomyces noursei" Eur. J. Biochem. vol. 269, pp. 347-357, 2002.

Inamori et al., "Antimicrobial Activity on Plant-Pathogenic Microorganisms and Phytogrowth-Inhibitory Activity of Streptothricin Antibiotics, Racemomycin-A and -C" Chem. Pharm. Bull. vol. 36, No. 4, pp. 1577-1580, 1988.

Taniyama et al., "Studies on the Inactivation and Regeneration of Streptothricin" J. Antibio. t. vol. 24, pp. 662-666, Oct. 1971.

* cited by examiner

*Primary Examiner*—Suzanne M Noakes
*Assistant Examiner*—Jae W Lee
(74) *Attorney, Agent, or Firm*—Hogan Lovells US LLP

(57) ABSTRACT

An enzyme capable of reducing the antibiotic activity (i.e., toxicity) of streptothricin with respect to eukaryotic cells without sacrificing antibiotic activity with respect to prokaryotic cells is provided along with a streptothricin derivative having reduced toxicity with respect to eukaryotic cells while retaining antibiotic activity with respect to prokaryotic cells, and a manufacturing method thereof. By opening the lactam ring of streptothricin, a protein having the amino acid sequence according to SEQ ID NO: 2, 4, 6, 8, 10, 12, 14 or 16 of the invention can reduce the antibiotic activity of streptothricin D with respect to eukaryotic cells without sacrificing antibiotic activity with respect to prokaryotic cells.

18 Claims, 4 Drawing Sheets

Fig. 2

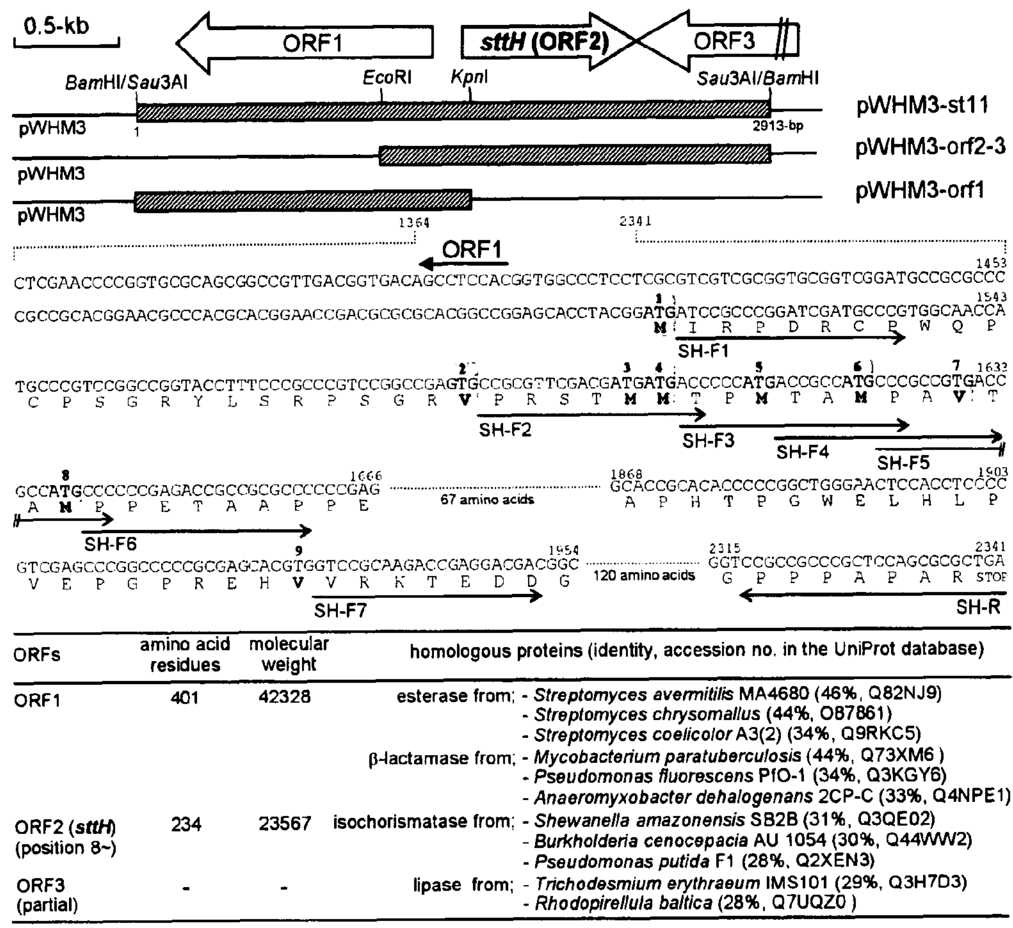

| ORFs | amino acid residues | molecular weight | homologous proteins (identity, accession no. in the UniProt database) | |
|---|---|---|---|---|
| ORF1 | 401 | 42328 | esterase from; | - *Streptomyces avermitilis* MA4680 (46%, Q82NJ9) |
| | | | | - *Streptomyces chrysomallus* (44%, O87861) |
| | | | | - *Streptomyces coelicolor* A3(2) (34%, Q9RKC5) |
| | | | β-lactamase from; | - *Mycobacterium paratuberculosis* (44%, Q73XM6 ) |
| | | | | - *Pseudomonas fluorescens* PfO-1 (34%, Q3KGY6) |
| | | | | - *Anaeromyxobacter dehalogenans* 2CP-C (33%, Q4NPE1) |
| ORF2 (***sttH***) (position 8~) | 234 | 23567 | isochorismatase from; | - *Shewanella amazonensis* SB2B (31%, Q3QE02) |
| | | | | - *Burkholderia cenocepacia* AU 1054 (30%, Q44WW2) |
| | | | | - *Pseudomonas putida* F1 (28%, Q2XEN3) |
| ORF3 (partial) | - | - | lipase from; | - *Trichodesmium erythraeum* IMS101 (29%, Q3H7D3) |
| | | | | - *Rhodopirellula baltica* (28%, Q7UQZ0 ) |

Fig. 4
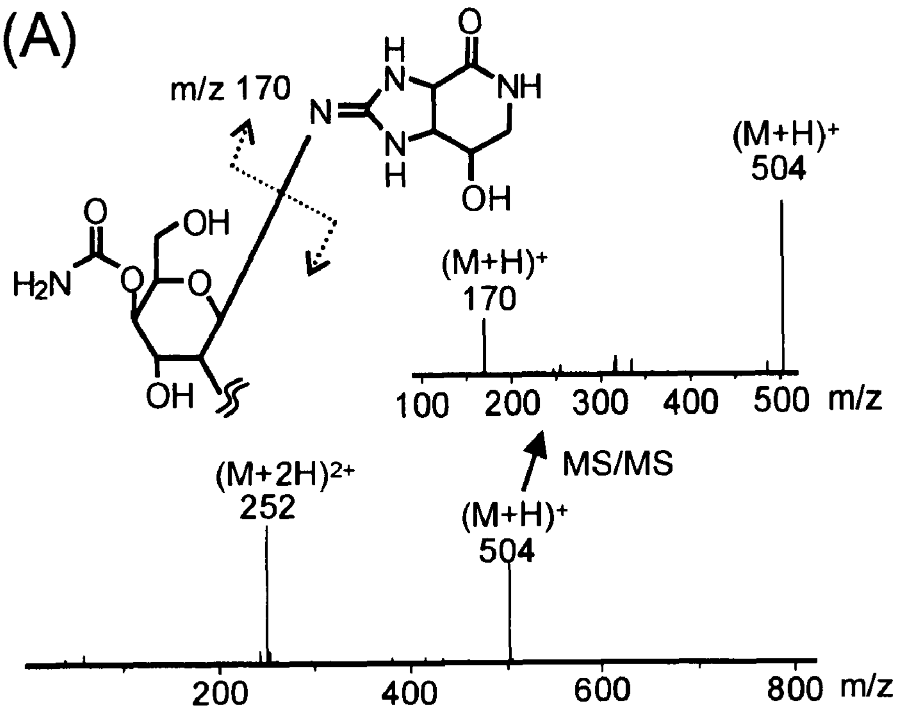
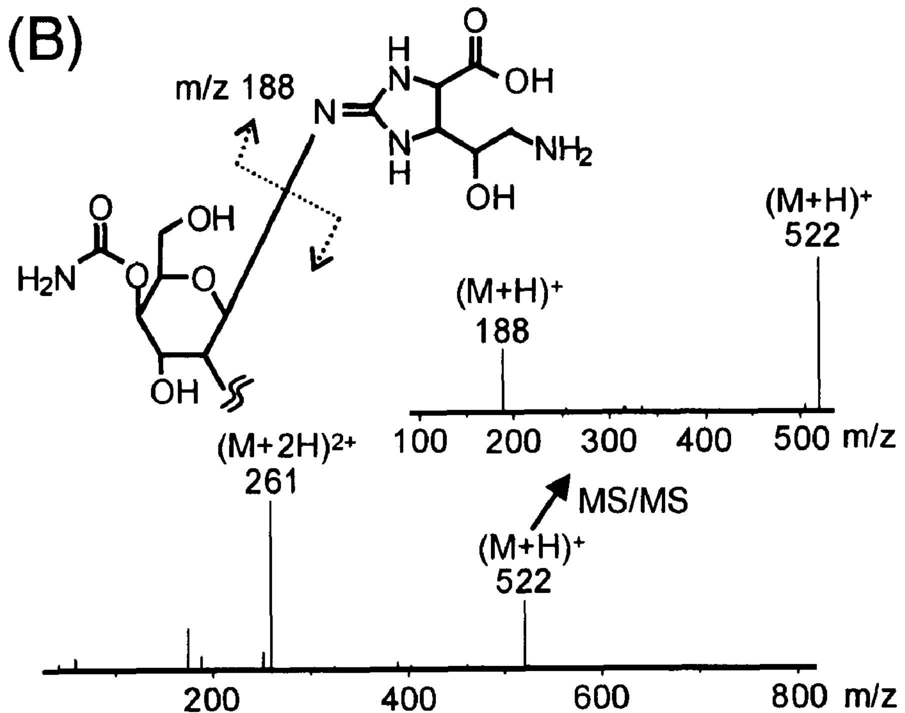

SEQUENCE LISTING

```
<160> NUMBER OF SEQ ID NOS: 26

<210> SEQ ID NO 1
<211> LENGTH: 705
<212> TYPE: DNA
<213> ORGANISM: Streptomyces albulus
<220> FEATURE:
<221> NAME/KEY: CDS
<222> LOCATION: (1)..(702)

<400> SEQUENCE: 1

atg ccc ccc gag acc gcc gcg ccc ccc gag acc gcc gcg ccc gcc cgg      48
Met Pro Pro Glu Thr Ala Ala Pro Pro Glu Thr Ala Ala Pro Ala Arg
1               5                   10                  15

ccg ctc cgc ccc gta cag gcc ctc ctc gtc gtc gac gtc caa acc gcg      96
Pro Leu Arg Pro Val Gln Ala Leu Leu Val Val Asp Val Gln Thr Ala
            20                  25                  30

ttc gtc tcc ggg gcc gag gcg gtc ccc gag gcg gcc cgg gtc ctg gac     144
Phe Val Ser Gly Ala Glu Ala Val Pro Glu Ala Ala Arg Val Leu Asp
        35                  40                  45

cgc acc cgt ggc ctg ctc gcc cgc gcc cgc acc gcc ggc gcc ctc gtc     192
Arg Thr Arg Gly Leu Leu Ala Arg Ala Arg Thr Ala Gly Ala Leu Val
    50                  55                  60

gtc cac ctc cag aac gac ggc gcg ccc ggc gcc gtc gac gca ccg cac     240
Val His Leu Gln Asn Asp Gly Ala Pro Gly Ala Val Asp Ala Pro His
65                  70                  75                  80

acc ccc ggc tgg gaa ctc cac ctc ccc gtc gag ccc ggc ccc cgc gag     288
Thr Pro Gly Trp Glu Leu His Leu Pro Val Glu Pro Gly Pro Arg Glu
                85                  90                  95

cac gtg gtc cgc aag acc gag gac gac ggc ttc gcg gac acc ggg ctc     336
His Val Val Arg Lys Thr Glu Asp Asp Gly Phe Ala Asp Thr Gly Leu
            100                 105                 110

ggc gcc ctg ctc gac gct gcg ggc gtg acc gaa ctg gcg gtg tgc ggg     384
Gly Ala Leu Leu Asp Ala Ala Gly Val Thr Glu Leu Ala Val Cys Gly
        115                 120                 125

gtg ctc tcc gaa atg tgc gtc gcc gcc acc gcg cgc acc gcc ctg gag     432
Val Leu Ser Glu Met Cys Val Ala Ala Thr Ala Arg Thr Ala Leu Glu
    130                 135                 140

ctg ggc cac cgc gtc gtc ctc ccg cac gac gcg cac gcc acc tac gac     480
Leu Gly His Arg Val Val Leu Pro His Asp Ala His Ala Thr Tyr Asp
145                 150                 155                 160

atc ccc gcc gcg ccc gac atc agc gac acc gtc ccg gcc gcg atg tcc     528
Ile Pro Ala Ala Pro Asp Ile Ser Asp Thr Val Pro Ala Ala Met Ser
                165                 170                 175

tcc cgg gcc gcg gag tgg gcc ctc ggc gac gag gtc gag atc gtc ccg     576
Ser Arg Ala Ala Glu Trp Ala Leu Gly Asp Glu Val Glu Ile Val Pro
            180                 185                 190

cgc gcc gcc gcg gtc ccc ttc gtc gcc ccg ccg ctg gcg ccc gcc ccc     624
Arg Ala Ala Ala Val Pro Phe Val Ala Pro Pro Leu Ala Pro Ala Pro
        195                 200                 205

gag gcc ccc gct gcc gcc gct gca ccc gcg gcc ggt acg ggg ctc agc     672
Glu Ala Pro Ala Ala Ala Ala Ala Pro Ala Ala Gly Thr Gly Leu Ser
    210                 215                 220

cct gct ggt ccg ccg ccc gct cca gcg cgc tga                         705
Pro Ala Gly Pro Pro Pro Ala Pro Ala Arg
225                 230
```

-continued

```
<210> SEQ ID NO 2
<211> LENGTH: 234
<212> TYPE: PRT
<213> ORGANISM: Streptomyces albulus

<400> SEQUENCE: 2

Met Pro Pro Glu Thr Ala Ala Pro Pro Glu Thr Ala Ala Pro Ala Arg
1               5                   10                  15

Pro Leu Arg Pro Val Gln Ala Leu Leu Val Val Asp Val Gln Thr Ala
            20                  25                  30

Phe Val Ser Gly Ala Glu Ala Val Pro Glu Ala Ala Arg Val Leu Asp
        35                  40                  45

Arg Thr Arg Gly Leu Leu Ala Arg Ala Arg Thr Ala Gly Ala Leu Val
    50                  55                  60

Val His Leu Gln Asn Asp Gly Ala Pro Gly Ala Val Asp Ala Pro His
65                  70                  75                  80

Thr Pro Gly Trp Glu Leu His Leu Pro Val Glu Pro Gly Pro Arg Glu
                85                  90                  95

His Val Val Arg Lys Thr Glu Asp Asp Gly Phe Ala Asp Thr Gly Leu
            100                 105                 110

Gly Ala Leu Leu Asp Ala Ala Gly Val Thr Glu Leu Ala Val Cys Gly
        115                 120                 125

Val Leu Ser Glu Met Cys Val Ala Ala Thr Ala Arg Thr Ala Leu Glu
    130                 135                 140

Leu Gly His Arg Val Val Leu Pro His Asp Ala His Ala Thr Tyr Asp
145                 150                 155                 160

Ile Pro Ala Ala Pro Asp Ile Ser Asp Thr Val Pro Ala Ala Met Ser
                165                 170                 175

Ser Arg Ala Ala Glu Trp Ala Leu Gly Asp Glu Val Glu Ile Val Pro
            180                 185                 190

Arg Ala Ala Ala Val Pro Phe Val Ala Pro Pro Leu Ala Pro Ala Pro
        195                 200                 205

Glu Ala Pro Ala Ala Ala Ala Ala Pro Ala Ala Gly Thr Gly Leu Ser
    210                 215                 220

Pro Ala Gly Pro Pro Pro Ala Pro Ala Arg
225                 230


<210> SEQ ID NO 3
<211> LENGTH: 714
<212> TYPE: DNA
<213> ORGANISM: streptomyces albulus
<220> FEATURE:
<221> NAME/KEY: CDS
<222> LOCATION: (1)..(711)

<400> SEQUENCE: 3

gtg acc gcc atg ccc ccc gag acc gcc gcg ccc ccc gag acc gcc gcg       48
Val Thr Ala Met Pro Pro Glu Thr Ala Ala Pro Pro Glu Thr Ala Ala
1               5                   10                  15

ccc gcc cgg ccg ctc cgc ccc gta cag gcc ctc ctc gtc gtc gac gtc       96
Pro Ala Arg Pro Leu Arg Pro Val Gln Ala Leu Leu Val Val Asp Val
            20                  25                  30

caa acc gcg ttc gtc tcc ggg gcc gag gcg gtc ccc gag gcg gcc cgg      144
Gln Thr Ala Phe Val Ser Gly Ala Glu Ala Val Pro Glu Ala Ala Arg
        35                  40                  45

gtc ctg gac cgc acc cgt ggc ctg ctc gcc cgc gcc cgc acc gcc ggc      192
Val Leu Asp Arg Thr Arg Gly Leu Leu Ala Arg Ala Arg Thr Ala Gly
    50                  55                  60
```

-continued

```
gcc ctc gtc gtc cac ctc cag aac gac ggc gcg ccc ggc gcc gtc gac      240
Ala Leu Val Val His Leu Gln Asn Asp Gly Ala Pro Gly Ala Val Asp
65                  70                  75                  80

gca ccg cac acc ccc ggc tgg gaa ctc cac ctc ccc gtc gag ccc ggc      288
Ala Pro His Thr Pro Gly Trp Glu Leu His Leu Pro Val Glu Pro Gly
                85                  90                  95

ccc cgc gag cac gtg gtc cgc aag acc gag gac gac ggc ttc gcg gac      336
Pro Arg Glu His Val Val Arg Lys Thr Glu Asp Asp Gly Phe Ala Asp
            100                 105                 110

acc ggg ctc ggc gcc ctg ctc gac gct gcg ggc gtg acc gaa ctg gcg      384
Thr Gly Leu Gly Ala Leu Leu Asp Ala Ala Gly Val Thr Glu Leu Ala
        115                 120                 125

gtg tgc ggg gtg ctc tcc gaa atg tgc gtc gcc gcc acc gcg cgc acc      432
Val Cys Gly Val Leu Ser Glu Met Cys Val Ala Ala Thr Ala Arg Thr
    130                 135                 140

gcc ctg gag ctg ggc cac cgc gtc gtc ctc ccg cac gac gcg cac gcc      480
Ala Leu Glu Leu Gly His Arg Val Val Leu Pro His Asp Ala His Ala
145                 150                 155                 160

acc tac gac atc ccc gcc gcg ccc gac atc agc gac acc gtc ccg gcc      528
Thr Tyr Asp Ile Pro Ala Ala Pro Asp Ile Ser Asp Thr Val Pro Ala
                165                 170                 175

gcg atg tcc tcc cgg gcc gcg gag tgg gcc ctc ggc gac gag gtc gag      576
Ala Met Ser Ser Arg Ala Ala Glu Trp Ala Leu Gly Asp Glu Val Glu
            180                 185                 190

atc gtc ccg cgc gcc gcc gcg gtc ccc ttc gtc gcc ccg ccg ctg gcg      624
Ile Val Pro Arg Ala Ala Ala Val Pro Phe Val Ala Pro Pro Leu Ala
        195                 200                 205

ccc gcc ccc gag gcc ccc gct gcc gcc gct gca ccc gcg gcc ggt acg      672
Pro Ala Pro Glu Ala Pro Ala Ala Ala Ala Ala Pro Ala Ala Gly Thr
    210                 215                 220

ggg ctc agc cct gct ggt ccg ccg ccc gct cca gcg cgc tga              714
Gly Leu Ser Pro Ala Gly Pro Pro Pro Ala Pro Ala Arg
225                 230                 235


<210> SEQ ID NO 4
<211> LENGTH: 237
<212> TYPE: PRT
<213> ORGANISM: streptomyces albulus

<400> SEQUENCE: 4

Val Thr Ala Met Pro Pro Glu Thr Ala Ala Pro Pro Glu Thr Ala Ala
1               5                   10                  15

Pro Ala Arg Pro Leu Arg Pro Val Gln Ala Leu Leu Val Val Asp Val
            20                  25                  30

Gln Thr Ala Phe Val Ser Gly Ala Glu Ala Val Pro Glu Ala Ala Arg
        35                  40                  45

Val Leu Asp Arg Thr Arg Gly Leu Leu Ala Arg Ala Arg Thr Ala Gly
    50                  55                  60

Ala Leu Val Val His Leu Gln Asn Asp Gly Ala Pro Gly Ala Val Asp
65                  70                  75                  80

Ala Pro His Thr Pro Gly Trp Glu Leu His Leu Pro Val Glu Pro Gly
                85                  90                  95

Pro Arg Glu His Val Val Arg Lys Thr Glu Asp Asp Gly Phe Ala Asp
            100                 105                 110

Thr Gly Leu Gly Ala Leu Leu Asp Ala Ala Gly Val Thr Glu Leu Ala
        115                 120                 125

Val Cys Gly Val Leu Ser Glu Met Cys Val Ala Ala Thr Ala Arg Thr
    130                 135                 140
```

```
Ala Leu Glu Leu Gly His Arg Val Val Leu Pro His Asp Ala His Ala
145                 150                 155                 160

Thr Tyr Asp Ile Pro Ala Ala Pro Asp Ile Ser Asp Thr Val Pro Ala
                165                 170                 175

Ala Met Ser Ser Arg Ala Ala Glu Trp Ala Leu Gly Asp Glu Val Glu
            180                 185                 190

Ile Val Pro Arg Ala Ala Ala Val Pro Phe Val Ala Pro Pro Leu Ala
        195                 200                 205

Pro Ala Pro Glu Ala Pro Ala Ala Ala Ala Ala Pro Ala Ala Gly Thr
    210                 215                 220

Gly Leu Ser Pro Ala Gly Pro Pro Pro Ala Pro Ala Arg
225                 230                 235


<210> SEQ ID NO 5
<211> LENGTH: 723
<212> TYPE: DNA
<213> ORGANISM: Streptomyces albulus
<220> FEATURE:
<221> NAME/KEY: CDS
<222> LOCATION: (1)..(720)

<400> SEQUENCE: 5

atg ccc gcc gtg acc gcc atg ccc ccc gag acc gcc gcg ccc ccc gag       48
Met Pro Ala Val Thr Ala Met Pro Pro Glu Thr Ala Ala Pro Pro Glu
1               5                   10                  15

acc gcc gcg ccc gcc cgg ccg ctc cgc ccc gta cag gcc ctc ctc gtc       96
Thr Ala Ala Pro Ala Arg Pro Leu Arg Pro Val Gln Ala Leu Leu Val
            20                  25                  30

gtc gac gtc caa acc gcg ttc gtc tcc ggg gcc gag gcg gtc ccc gag      144
Val Asp Val Gln Thr Ala Phe Val Ser Gly Ala Glu Ala Val Pro Glu
        35                  40                  45

gcg gcc cgg gtc ctg gac cgc acc cgt ggc ctg ctc gcc cgc gcc cgc      192
Ala Ala Arg Val Leu Asp Arg Thr Arg Gly Leu Leu Ala Arg Ala Arg
    50                  55                  60

acc gcc ggc gcc ctc gtc gtc cac ctc cag aac gac ggc gcg ccc ggc      240
Thr Ala Gly Ala Leu Val Val His Leu Gln Asn Asp Gly Ala Pro Gly
65                  70                  75                  80

gcc gtc gac gca ccg cac acc ccc ggc tgg gaa ctc cac ctc ccc gtc      288
Ala Val Asp Ala Pro His Thr Pro Gly Trp Glu Leu His Leu Pro Val
                85                  90                  95

gag ccc ggc ccc cgc gag cac gtg gtc cgc aag acc gag gac gac ggc      336
Glu Pro Gly Pro Arg Glu His Val Val Arg Lys Thr Glu Asp Asp Gly
            100                 105                 110

ttc gcg gac acc ggg ctc ggc gcc ctg ctc gac gct gcg ggc gtg acc      384
Phe Ala Asp Thr Gly Leu Gly Ala Leu Leu Asp Ala Ala Gly Val Thr
        115                 120                 125

gaa ctg gcg gtg tgc ggg gtg ctc tcc gaa atg tgc gtc gcc gcc acc      432
Glu Leu Ala Val Cys Gly Val Leu Ser Glu Met Cys Val Ala Ala Thr
    130                 135                 140

gcg cgc acc gcc ctg gag ctg ggc cac cgc gtc gtc ctc ccg cac gac      480
Ala Arg Thr Ala Leu Glu Leu Gly His Arg Val Val Leu Pro His Asp
145                 150                 155                 160

gcg cac gcc acc tac gac atc ccc gcc gcg ccc gac atc agc gac acc      528
Ala His Ala Thr Tyr Asp Ile Pro Ala Ala Pro Asp Ile Ser Asp Thr
                165                 170                 175

gtc ccg gcc gcg atg tcc tcc cgg gcc gcg gag tgg gcc ctc ggc gac      576
Val Pro Ala Ala Met Ser Ser Arg Ala Ala Glu Trp Ala Leu Gly Asp
            180                 185                 190
```

-continued

```
gag gtc gag atc gtc ccg cgc gcc gcc gcg gtc ccc ttc gtc gcc ccg      624
Glu Val Glu Ile Val Pro Arg Ala Ala Ala Val Pro Phe Val Ala Pro
        195                 200                 205

ccg ctg gcg ccc gcc ccc gag gcc ccc gct gcc gcc gct gca ccc gcg      672
Pro Leu Ala Pro Ala Pro Glu Ala Pro Ala Ala Ala Ala Ala Pro Ala
    210                 215                 220

gcc ggt acg ggg ctc agc cct gct ggt ccg ccg ccc gct cca gcg cgc      720
Ala Gly Thr Gly Leu Ser Pro Ala Gly Pro Pro Pro Ala Pro Ala Arg
225                 230                 235                 240

tgs                                                                  723


<210> SEQ ID NO 6
<211> LENGTH: 240
<212> TYPE: PRT
<213> ORGANISM: Streptomyces albulus

<400> SEQUENCE: 6

Met Pro Ala Val Thr Ala Met Pro Pro Glu Thr Ala Ala Pro Pro Glu
1               5                   10                  15

Thr Ala Ala Pro Ala Arg Pro Leu Arg Pro Val Gln Ala Leu Leu Val
            20                  25                  30

Val Asp Val Gln Thr Ala Phe Val Ser Gly Ala Glu Ala Val Pro Glu
        35                  40                  45

Ala Ala Arg Val Leu Asp Arg Thr Arg Gly Leu Leu Ala Arg Ala Arg
    50                  55                  60

Thr Ala Gly Ala Leu Val Val His Leu Gln Asn Asp Gly Ala Pro Gly
65                  70                  75                  80

Ala Val Asp Ala Pro His Thr Pro Gly Trp Glu Leu His Leu Pro Val
                85                  90                  95

Glu Pro Gly Pro Arg Glu His Val Val Arg Lys Thr Glu Asp Asp Gly
            100                 105                 110

Phe Ala Asp Thr Gly Leu Gly Ala Leu Leu Asp Ala Ala Gly Val Thr
        115                 120                 125

Glu Leu Ala Val Cys Gly Val Leu Ser Glu Met Cys Val Ala Ala Thr
    130                 135                 140

Ala Arg Thr Ala Leu Glu Leu Gly His Arg Val Val Leu Pro His Asp
145                 150                 155                 160

Ala His Ala Thr Tyr Asp Ile Pro Ala Ala Pro Asp Ile Ser Asp Thr
                165                 170                 175

Val Pro Ala Ala Met Ser Ser Arg Ala Ala Glu Trp Ala Leu Gly Asp
            180                 185                 190

Glu Val Glu Ile Val Pro Arg Ala Ala Ala Val Pro Phe Val Ala Pro
        195                 200                 205

Pro Leu Ala Pro Ala Pro Glu Ala Pro Ala Ala Ala Ala Ala Pro Ala
    210                 215                 220

Ala Gly Thr Gly Leu Ser Pro Ala Gly Pro Pro Pro Ala Pro Ala Arg
225                 230                 235                 240


<210> SEQ ID NO 7
<211> LENGTH: 732
<212> TYPE: DNA
<213> ORGANISM: Streptomyces albulus
<220> FEATURE:
<221> NAME/KEY: CDS
<222> LOCATION: (1)..(729)
```

```
<400> SEQUENCE: 7

atg acc gcc atg ccc gcc gtg acc gcc atg ccc ccc gag acc gcc gcg       48
Met Thr Ala Met Pro Ala Val Thr Ala Met Pro Pro Glu Thr Ala Ala
1               5                   10                  15

ccc ccc gag acc gcc gcg ccc gcc cgg ccg ctc cgc ccc gta cag gcc       96
Pro Pro Glu Thr Ala Ala Pro Ala Arg Pro Leu Arg Pro Val Gln Ala
            20                  25                  30

ctc ctc gtc gtc gac gtc caa acc gcg ttc gtc tcc ggg gcc gag gcg      144
Leu Leu Val Val Asp Val Gln Thr Ala Phe Val Ser Gly Ala Glu Ala
        35                  40                  45

gtc ccc gag gcg gcc cgg gtc ctg gac cgc acc cgt ggc ctg ctc gcc      192
Val Pro Glu Ala Ala Arg Val Leu Asp Arg Thr Arg Gly Leu Leu Ala
    50                  55                  60

cgc gcc cgc acc gcc ggc gcc ctc gtc gtc cac ctc cag aac gac ggc      240
Arg Ala Arg Thr Ala Gly Ala Leu Val Val His Leu Gln Asn Asp Gly
65                  70                  75                  80

gcg ccc ggc gcc gtc gac gca ccg cac acc ccc ggc tgg gaa ctc cac      288
Ala Pro Gly Ala Val Asp Ala Pro His Thr Pro Gly Trp Glu Leu His
                85                  90                  95

ctc ccc gtc gag ccc ggc ccc cgc gag cac gtg gtc cgc aag acc gag      336
Leu Pro Val Glu Pro Gly Pro Arg Glu His Val Val Arg Lys Thr Glu
            100                 105                 110

gac gac ggc ttc gcg gac acc ggg ctc ggc gcc ctg ctc gac gct gcg      384
Asp Asp Gly Phe Ala Asp Thr Gly Leu Gly Ala Leu Leu Asp Ala Ala
        115                 120                 125

ggc gtg acc gaa ctg gcg gtg tgc ggg gtg ctc tcc gaa atg tgc gtc      432
Gly Val Thr Glu Leu Ala Val Cys Gly Val Leu Ser Glu Met Cys Val
    130                 135                 140

gcc gcc acc gcg cgc acc gcc ctg gag ctg ggc cac cgc gtc gtc ctc      480
Ala Ala Thr Ala Arg Thr Ala Leu Glu Leu Gly His Arg Val Val Leu
145                 150                 155                 160

ccg cac gac gcg cac gcc acc tac gac atc ccc gcc gcg ccc gac atc      528
Pro His Asp Ala His Ala Thr Tyr Asp Ile Pro Ala Ala Pro Asp Ile
                165                 170                 175

agc gac acc gtc ccg gcc gcg atg tcc tcc cgg gcc gcg gag tgg gcc      576
Ser Asp Thr Val Pro Ala Ala Met Ser Ser Arg Ala Ala Glu Trp Ala
            180                 185                 190

ctc ggc gac gag gtc gag atc gtc ccg cgc gcc gcc gcg gtc ccc ttc      624
Leu Gly Asp Glu Val Glu Ile Val Pro Arg Ala Ala Ala Val Pro Phe
        195                 200                 205

gtc gcc ccg ccg ctg gcg ccc gcc ccc gag gcc ccc gct gcc gcc gct      672
Val Ala Pro Pro Leu Ala Pro Ala Pro Glu Ala Pro Ala Ala Ala Ala
    210                 215                 220

gca ccc gcg gcc ggt acg ggg ctc agc cct gct ggt ccg ccg ccc gct      720
Ala Pro Ala Ala Gly Thr Gly Leu Ser Pro Ala Gly Pro Pro Pro Ala
225                 230                 235                 240

cca gcg cgc tga                                                      732
Pro Ala Arg


<210> SEQ ID NO 8
<211> LENGTH: 243
<212> TYPE: PRT
<213> ORGANISM: Streptomyces albulus

<400> SEQUENCE: 8

Met Thr Ala Met Pro Ala Val Thr Ala Met Pro Pro Glu Thr Ala Ala
1               5                   10                  15

Pro Pro Glu Thr Ala Ala Pro Ala Arg Pro Leu Arg Pro Val Gln Ala
            20                  25                  30
```

-continued

```
Leu Leu Val Val Asp Val Gln Thr Ala Phe Val Ser Gly Ala Glu Ala
        35                  40                  45

Val Pro Glu Ala Ala Arg Val Leu Asp Arg Thr Arg Gly Leu Leu Ala
    50                  55                  60

Arg Ala Arg Thr Ala Gly Ala Leu Val Val His Leu Gln Asn Asp Gly
65                  70                  75                  80

Ala Pro Gly Ala Val Asp Ala Pro His Thr Pro Gly Trp Glu Leu His
                85                  90                  95

Leu Pro Val Glu Pro Gly Pro Arg Glu His Val Val Arg Lys Thr Glu
            100                 105                 110

Asp Asp Gly Phe Ala Asp Thr Gly Leu Gly Ala Leu Leu Asp Ala Ala
        115                 120                 125

Gly Val Thr Glu Leu Ala Val Cys Gly Val Leu Ser Glu Met Cys Val
    130                 135                 140

Ala Ala Thr Ala Arg Thr Ala Leu Glu Leu Gly His Arg Val Val Leu
145                 150                 155                 160

Pro His Asp Ala His Ala Thr Tyr Asp Ile Pro Ala Ala Pro Asp Ile
                165                 170                 175

Ser Asp Thr Val Pro Ala Ala Met Ser Ser Arg Ala Ala Glu Trp Ala
            180                 185                 190

Leu Gly Asp Glu Val Glu Ile Val Pro Arg Ala Ala Ala Val Pro Phe
        195                 200                 205

Val Ala Pro Pro Leu Ala Pro Ala Pro Glu Ala Pro Ala Ala Ala Ala
    210                 215                 220

Ala Pro Ala Ala Gly Thr Gly Leu Ser Pro Ala Gly Pro Pro Pro Ala
225                 230                 235                 240

Pro Ala Arg


<210> SEQ ID NO 9
<211> LENGTH: 741
<212> TYPE: DNA
<213> ORGANISM: Streptomyces albulus
<220> FEATURE:
<221> NAME/KEY: CDS
<222> LOCATION: (1)..(738)

<400> SEQUENCE: 9

atg acc ccc atg acc gcc atg ccc gcc gtg acc gcc atg ccc ccc gag       48
Met Thr Pro Met Thr Ala Met Pro Ala Val Thr Ala Met Pro Pro Glu
1               5                   10                  15

acc gcc gcg ccc ccc gag acc gcc gcg ccc gcc cgg ccg ctc cgc ccc       96
Thr Ala Ala Pro Pro Glu Thr Ala Ala Pro Ala Arg Pro Leu Arg Pro
            20                  25                  30

gta cag gcc ctc ctc gtc gtc gac gtc caa acc gcg ttc gtc tcc ggg      144
Val Gln Ala Leu Leu Val Val Asp Val Gln Thr Ala Phe Val Ser Gly
        35                  40                  45

gcc gag gcg gtc ccc gag gcg gcc cgg gtc ctg gac cgc acc cgt ggc      192
Ala Glu Ala Val Pro Glu Ala Ala Arg Val Leu Asp Arg Thr Arg Gly
    50                  55                  60

ctg ctc gcc cgc gcc cgc acc gcc ggc gcc ctc gtc gtc cac ctc cag      240
Leu Leu Ala Arg Ala Arg Thr Ala Gly Ala Leu Val Val His Leu Gln
65                  70                  75                  80

aac gac ggc gcg ccc ggc gcc gtc gac gca ccg cac acc ccc ggc tgg      288
Asn Asp Gly Ala Pro Gly Ala Val Asp Ala Pro His Thr Pro Gly Trp
                85                  90                  95

gaa ctc cac ctc ccc gtc gag ccc ggc ccc cgc gag cac gtg gtc cgc      336
Glu Leu His Leu Pro Val Glu Pro Gly Pro Arg Glu His Val Val Arg
            100                 105                 110
```

-continued

```
aag acc gag gac gac ggc ttc gcg gac acc ggg ctc ggc gcc ctg ctc      384
Lys Thr Glu Asp Asp Gly Phe Ala Asp Thr Gly Leu Gly Ala Leu Leu
        115                 120                 125

gac gct gcg ggc gtg acc gaa ctg gcg gtg tgc ggg gtg ctc tcc gaa      432
Asp Ala Ala Gly Val Thr Glu Leu Ala Val Cys Gly Val Leu Ser Glu
    130                 135                 140

atg tgc gtc gcc gcc acc gcg cgc acc gcc ctg gag ctg ggc cac cgc      480
Met Cys Val Ala Ala Thr Ala Arg Thr Ala Leu Glu Leu Gly His Arg
145                 150                 155                 160

gtc gtc ctc ccg cac gac gcg cac gcc acc tac gac atc ccc gcc gcg      528
Val Val Leu Pro His Asp Ala His Ala Thr Tyr Asp Ile Pro Ala Ala
                165                 170                 175

ccc gac atc agc gac acc gtc ccg gcc gcg atg tcc tcc cgg gcc gcg      576
Pro Asp Ile Ser Asp Thr Val Pro Ala Ala Met Ser Ser Arg Ala Ala
            180                 185                 190

gag tgg gcc ctc ggc gac gag gtc gag atc gtc ccg cgc gcc gcc gcg      624
Glu Trp Ala Leu Gly Asp Glu Val Glu Ile Val Pro Arg Ala Ala Ala
        195                 200                 205

gtc ccc ttc gtc gcc ccg ccg ctg gcg ccc gcc ccc gag gcc ccc gct      672
Val Pro Phe Val Ala Pro Pro Leu Ala Pro Ala Pro Glu Ala Pro Ala
    210                 215                 220

gcc gcc gct gca ccc gcg gcc ggt acg ggg ctc agc cct gct ggt ccg      720
Ala Ala Ala Ala Pro Ala Ala Gly Thr Gly Leu Ser Pro Ala Gly Pro
225                 230                 235                 240

ccg ccc gct cca gcg cgc tga                                          741
Pro Pro Ala Pro Ala Arg
                245


<210> SEQ ID NO 10
<211> LENGTH: 246
<212> TYPE: PRT
<213> ORGANISM: Streptomyces albulus

<400> SEQUENCE: 10

Met Thr Pro Met Thr Ala Met Pro Ala Val Thr Ala Met Pro Pro Glu
1               5                   10                  15

Thr Ala Ala Pro Pro Glu Thr Ala Ala Pro Ala Arg Pro Leu Arg Pro
            20                  25                  30

Val Gln Ala Leu Leu Val Val Asp Val Gln Thr Ala Phe Val Ser Gly
        35                  40                  45

Ala Glu Ala Val Pro Glu Ala Ala Arg Val Leu Asp Arg Thr Arg Gly
    50                  55                  60

Leu Leu Ala Arg Ala Arg Thr Ala Gly Ala Leu Val Val His Leu Gln
65                  70                  75                  80

Asn Asp Gly Ala Pro Gly Ala Val Asp Ala Pro His Thr Pro Gly Trp
                85                  90                  95

Glu Leu His Leu Pro Val Glu Pro Gly Pro Arg Glu His Val Val Arg
            100                 105                 110

Lys Thr Glu Asp Asp Gly Phe Ala Asp Thr Gly Leu Gly Ala Leu Leu
        115                 120                 125

Asp Ala Ala Gly Val Thr Glu Leu Ala Val Cys Gly Val Leu Ser Glu
    130                 135                 140

Met Cys Val Ala Ala Thr Ala Arg Thr Ala Leu Glu Leu Gly His Arg
145                 150                 155                 160

Val Val Leu Pro His Asp Ala His Ala Thr Tyr Asp Ile Pro Ala Ala
                165                 170                 175

Pro Asp Ile Ser Asp Thr Val Pro Ala Ala Met Ser Ser Arg Ala Ala
            180                 185                 190
```

-continued

```
Glu Trp Ala Leu Gly Asp Glu Val Glu Ile Val Pro Arg Ala Ala Ala
        195                 200                 205

Val Pro Phe Val Ala Pro Pro Leu Ala Pro Ala Pro Glu Ala Pro Ala
    210                 215                 220

Ala Ala Ala Ala Pro Ala Ala Gly Thr Gly Leu Ser Pro Ala Gly Pro
225                 230                 235                 240

Pro Pro Ala Pro Ala Arg
                245


<210> SEQ ID NO 11
<211> LENGTH: 744
<212> TYPE: DNA
<213> ORGANISM: Streptomyces albulus
<220> FEATURE:
<221> NAME/KEY: CDS
<222> LOCATION: (1)..(741)

<400> SEQUENCE: 11

atg atg acc ccc atg acc gcc atg ccc gcc gtg acc gcc atg ccc ccc       48
Met Met Thr Pro Met Thr Ala Met Pro Ala Val Thr Ala Met Pro Pro
1               5                   10                  15

gag acc gcc gcg ccc ccc gag acc gcc gcg ccc gcc cgg ccg ctc cgc       96
Glu Thr Ala Ala Pro Pro Glu Thr Ala Ala Pro Ala Arg Pro Leu Arg
            20                  25                  30

ccc gta cag gcc ctc ctc gtc gtc gac gtc caa acc gcg ttc gtc tcc      144
Pro Val Gln Ala Leu Leu Val Val Asp Val Gln Thr Ala Phe Val Ser
        35                  40                  45

ggg gcc gag gcg gtc ccc gag gcg gcc cgg gtc ctg gac cgc acc cgt      192
Gly Ala Glu Ala Val Pro Glu Ala Ala Arg Val Leu Asp Arg Thr Arg
    50                  55                  60

ggc ctg ctc gcc cgc gcc cgc acc gcc ggc gcc ctc gtc gtc cac ctc      240
Gly Leu Leu Ala Arg Ala Arg Thr Ala Gly Ala Leu Val Val His Leu
65                  70                  75                  80

cag aac gac ggc gcg ccc ggc gcc gtc gac gca ccg cac acc ccc ggc      288
Gln Asn Asp Gly Ala Pro Gly Ala Val Asp Ala Pro His Thr Pro Gly
                85                  90                  95

tgg gaa ctc cac ctc ccc gtc gag ccc ggc ccc cgc gag cac gtg gtc      336
Trp Glu Leu His Leu Pro Val Glu Pro Gly Pro Arg Glu His Val Val
            100                 105                 110

cgc aag acc gag gac gac ggc ttc gcg gac acc ggg ctc ggc gcc ctg      384
Arg Lys Thr Glu Asp Asp Gly Phe Ala Asp Thr Gly Leu Gly Ala Leu
        115                 120                 125

ctc gac gct gcg ggc gtg acc gaa ctg gcg gtg tgc ggg gtg ctc tcc      432
Leu Asp Ala Ala Gly Val Thr Glu Leu Ala Val Cys Gly Val Leu Ser
    130                 135                 140

gaa atg tgc gtc gcc gcc acc gcg cgc acc gcc ctg gag ctg ggc cac      480
Glu Met Cys Val Ala Ala Thr Ala Arg Thr Ala Leu Glu Leu Gly His
145                 150                 155                 160

cgc gtc gtc ctc ccg cac gac gcg cac gcc acc tac gac atc ccc gcc      528
Arg Val Val Leu Pro His Asp Ala His Ala Thr Tyr Asp Ile Pro Ala
                165                 170                 175

gcg ccc gac atc agc gac acc gtc ccg gcc gcg atg tcc tcc cgg gcc      576
Ala Pro Asp Ile Ser Asp Thr Val Pro Ala Ala Met Ser Ser Arg Ala
            180                 185                 190

gcg gag tgg gcc ctc ggc gac gag gtc gag atc gtc ccg cgc gcc gcc      624
Ala Glu Trp Ala Leu Gly Asp Glu Val Glu Ile Val Pro Arg Ala Ala
        195                 200                 205

gcg gtc ccc ttc gtc gcc ccg ccg ctg gcg ccc gcc ccc gag gcc ccc      672
Ala Val Pro Phe Val Ala Pro Pro Leu Ala Pro Ala Pro Glu Ala Pro
    210                 215                 220
```

-continued

```
gct gcc gcc gct gca ccc gcg gcc ggt acg ggg ctc agc cct gct ggt      720
Ala Ala Ala Ala Ala Pro Ala Ala Gly Thr Gly Leu Ser Pro Ala Gly
225                 230                 235                 240

ccg ccg ccc gct cca gcg cgc tga                                      744
Pro Pro Pro Ala Pro Ala Arg
                245


<210> SEQ ID NO 12
<211> LENGTH: 247
<212> TYPE: PRT
<213> ORGANISM: Streptomyces albulus

<400> SEQUENCE: 12

Met Met Thr Pro Met Thr Ala Met Pro Ala Val Thr Ala Met Pro Pro
1               5                   10                  15

Glu Thr Ala Ala Pro Pro Glu Thr Ala Ala Pro Ala Arg Pro Leu Arg
            20                  25                  30

Pro Val Gln Ala Leu Leu Val Val Asp Val Gln Thr Ala Phe Val Ser
        35                  40                  45

Gly Ala Glu Ala Val Pro Glu Ala Ala Arg Val Leu Asp Arg Thr Arg
    50                  55                  60

Gly Leu Leu Ala Arg Ala Arg Thr Ala Gly Ala Leu Val Val His Leu
65                  70                  75                  80

Gln Asn Asp Gly Ala Pro Gly Ala Val Asp Ala Pro His Thr Pro Gly
                85                  90                  95

Trp Glu Leu His Leu Pro Val Glu Pro Gly Pro Arg Glu His Val Val
            100                 105                 110

Arg Lys Thr Glu Asp Asp Gly Phe Ala Asp Thr Gly Leu Gly Ala Leu
        115                 120                 125

Leu Asp Ala Ala Gly Val Thr Glu Leu Ala Val Cys Gly Val Leu Ser
    130                 135                 140

Glu Met Cys Val Ala Ala Thr Ala Arg Thr Ala Leu Glu Leu Gly His
145                 150                 155                 160

Arg Val Val Leu Pro His Asp Ala His Ala Thr Tyr Asp Ile Pro Ala
                165                 170                 175

Ala Pro Asp Ile Ser Asp Thr Val Pro Ala Ala Met Ser Ser Arg Ala
            180                 185                 190

Ala Glu Trp Ala Leu Gly Asp Glu Val Glu Ile Val Pro Arg Ala Ala
        195                 200                 205

Ala Val Pro Phe Val Ala Pro Pro Leu Ala Pro Ala Pro Glu Ala Pro
    210                 215                 220

Ala Ala Ala Ala Ala Pro Ala Ala Gly Thr Gly Leu Ser Pro Ala Gly
225                 230                 235                 240

Pro Pro Pro Ala Pro Ala Arg
                245


<210> SEQ ID NO 13
<211> LENGTH: 759
<212> TYPE: DNA
<213> ORGANISM: Streptomyces albulus
<220> FEATURE:
<221> NAME/KEY: CDS
<222> LOCATION: (1)..(756)

<400> SEQUENCE: 13

gtg ccg cgt tcg acg atg atg acc ccc atg acc gcc atg ccc gcc gtg       48
Val Pro Arg Ser Thr Met Met Thr Pro Met Thr Ala Met Pro Ala Val
1               5                   10                  15
```

-continued

```
acc gcc atg ccc ccc gag acc gcc gcg ccc ccc gag acc gcc gcg ccc        96
Thr Ala Met Pro Pro Glu Thr Ala Ala Pro Pro Glu Thr Ala Ala Pro
            20                  25                  30

gcc cgg ccg ctc cgc ccc gta cag gcc ctc ctc gtc gtc gac gtc caa       144
Ala Arg Pro Leu Arg Pro Val Gln Ala Leu Leu Val Val Asp Val Gln
        35                  40                  45

acc gcg ttc gtc tcc ggg gcc gag gcg gtc ccc gag gcg gcc cgg gtc       192
Thr Ala Phe Val Ser Gly Ala Glu Ala Val Pro Glu Ala Ala Arg Val
    50                  55                  60

ctg gac cgc acc cgt ggc ctg ctc gcc cgc gcc cgc acc gcc ggc gcc       240
Leu Asp Arg Thr Arg Gly Leu Leu Ala Arg Ala Arg Thr Ala Gly Ala
65                  70                  75                  80

ctc gtc gtc cac ctc cag aac gac ggc gcg ccc ggc gcc gtc gac gca       288
Leu Val Val His Leu Gln Asn Asp Gly Ala Pro Gly Ala Val Asp Ala
                85                  90                  95

ccg cac acc ccc ggc tgg gaa ctc cac ctc ccc gtc gag ccc ggc ccc       336
Pro His Thr Pro Gly Trp Glu Leu His Leu Pro Val Glu Pro Gly Pro
            100                 105                 110

cgc gag cac gtg gtc cgc aag acc gag gac gac ggc ttc gcg gac acc       384
Arg Glu His Val Val Arg Lys Thr Glu Asp Asp Gly Phe Ala Asp Thr
        115                 120                 125

ggg ctc ggc gcc ctg ctc gac gct gcg ggc gtg acc gaa ctg gcg gtg       432
Gly Leu Gly Ala Leu Leu Asp Ala Ala Gly Val Thr Glu Leu Ala Val
    130                 135                 140

tgc ggg gtg ctc tcc gaa atg tgc gtc gcc gcc acc gcg cgc acc gcc       480
Cys Gly Val Leu Ser Glu Met Cys Val Ala Ala Thr Ala Arg Thr Ala
145                 150                 155                 160

ctg gag ctg ggc cac cgc gtc gtc ctc ccg cac gac gcg cac gcc acc       528
Leu Glu Leu Gly His Arg Val Val Leu Pro His Asp Ala His Ala Thr
                165                 170                 175

tac gac atc ccc gcc gcg ccc gac atc agc gac acc gtc ccg gcc gcg       576
Tyr Asp Ile Pro Ala Ala Pro Asp Ile Ser Asp Thr Val Pro Ala Ala
            180                 185                 190

atg tcc tcc cgg gcc gcg gag tgg gcc ctc ggc gac gag gtc gag atc       624
Met Ser Ser Arg Ala Ala Glu Trp Ala Leu Gly Asp Glu Val Glu Ile
        195                 200                 205

gtc ccg cgc gcc gcc gcg gtc ccc ttc gtc gcc ccg ccg ctg gcg ccc       672
Val Pro Arg Ala Ala Ala Val Pro Phe Val Ala Pro Pro Leu Ala Pro
    210                 215                 220

gcc ccc gag gcc ccc gct gcc gcc gct gca ccc gcg gcc ggt acg ggg       720
Ala Pro Glu Ala Pro Ala Ala Ala Ala Ala Pro Ala Ala Gly Thr Gly
225                 230                 235                 240

ctc agc cct gct ggt ccg ccg ccc gct cca gcg cgc tga                   759
Leu Ser Pro Ala Gly Pro Pro Pro Ala Pro Ala Arg
                245                 250


<210> SEQ ID NO 14
<211> LENGTH: 252
<212> TYPE: PRT
<213> ORGANISM: Streptomyces albulus

<400> SEQUENCE: 14

Val Pro Arg Ser Thr Met Met Thr Pro Met Thr Ala Met Pro Ala Val
1               5                   10                  15

Thr Ala Met Pro Pro Glu Thr Ala Ala Pro Pro Glu Thr Ala Ala Pro
            20                  25                  30

Ala Arg Pro Leu Arg Pro Val Gln Ala Leu Leu Val Val Asp Val Gln
        35                  40                  45

Thr Ala Phe Val Ser Gly Ala Glu Ala Val Pro Glu Ala Ala Arg Val
    50                  55                  60
```

```
Leu Asp Arg Thr Arg Gly Leu Leu Ala Arg Ala Arg Thr Ala Gly Ala
65                  70                  75                  80

Leu Val Val His Leu Gln Asn Asp Gly Ala Pro Gly Ala Val Asp Ala
                85                  90                  95

Pro His Thr Pro Gly Trp Glu Leu His Leu Pro Val Glu Pro Gly Pro
            100                 105                 110

Arg Glu His Val Val Arg Lys Thr Glu Asp Asp Gly Phe Ala Asp Thr
        115                 120                 125

Gly Leu Gly Ala Leu Leu Asp Ala Ala Gly Val Thr Glu Leu Ala Val
    130                 135                 140

Cys Gly Val Leu Ser Glu Met Cys Val Ala Ala Thr Ala Arg Thr Ala
145                 150                 155                 160

Leu Glu Leu Gly His Arg Val Val Leu Pro His Asp Ala His Ala Thr
                165                 170                 175

Tyr Asp Ile Pro Ala Ala Pro Asp Ile Ser Asp Thr Val Pro Ala Ala
            180                 185                 190

Met Ser Ser Arg Ala Ala Glu Trp Ala Leu Gly Asp Glu Val Glu Ile
        195                 200                 205

Val Pro Arg Ala Ala Ala Val Pro Phe Val Ala Pro Pro Leu Ala Pro
    210                 215                 220

Ala Pro Glu Ala Pro Ala Ala Ala Ala Ala Pro Ala Ala Gly Thr Gly
225                 230                 235                 240

Leu Ser Pro Ala Gly Pro Pro Pro Ala Pro Ala Arg
                245                 250


<210> SEQ ID NO 15
<211> LENGTH: 831
<212> TYPE: DNA
<213> ORGANISM: Streptomyces albulus
<220> FEATURE:
<221> NAME/KEY: CDS
<222> LOCATION: (1)..(828)

<400> SEQUENCE: 15

atg atc cgc ccg gat cga tgc ccg tgg caa cca tgc ccg tcc ggc cgg       48
Met Ile Arg Pro Asp Arg Cys Pro Trp Gln Pro Cys Pro Ser Gly Arg
1               5                   10                  15

tac ctt tcc cgc ccg tcc ggc cga gtg ccg cgt tcg acg atg atg acc       96
Tyr Leu Ser Arg Pro Ser Gly Arg Val Pro Arg Ser Thr Met Met Thr
            20                  25                  30

ccc atg acc gcc atg ccc gcc gtg acc gcc atg ccc ccc gag acc gcc      144
Pro Met Thr Ala Met Pro Ala Val Thr Ala Met Pro Pro Glu Thr Ala
        35                  40                  45

gcg ccc ccc gag acc gcc gcg ccc gcc cgg ccg ctc cgc ccc gta cag      192
Ala Pro Pro Glu Thr Ala Ala Pro Ala Arg Pro Leu Arg Pro Val Gln
    50                  55                  60

gcc ctc ctc gtc gtc gac gtc caa acc gcg ttc gtc tcc ggg gcc gag      240
Ala Leu Leu Val Val Asp Val Gln Thr Ala Phe Val Ser Gly Ala Glu
65                  70                  75                  80

gcg gtc ccc gag gcg gcc cgg gtc ctg gac cgc acc cgt ggc ctg ctc      288
Ala Val Pro Glu Ala Ala Arg Val Leu Asp Arg Thr Arg Gly Leu Leu
                85                  90                  95

gcc cgc gcc cgc acc gcc ggc gcc ctc gtc gtc cac ctc cag aac gac      336
Ala Arg Ala Arg Thr Ala Gly Ala Leu Val Val His Leu Gln Asn Asp
            100                 105                 110

ggc gcg ccc ggc gcc gtc gac gca ccg cac acc ccc ggc tgg gaa ctc      384
Gly Ala Pro Gly Ala Val Asp Ala Pro His Thr Pro Gly Trp Glu Leu
        115                 120                 125
```

```
cac ctc ccc gtc gag ccc ggc ccc cgc gag cac gtg gtc cgc aag acc      432
His Leu Pro Val Glu Pro Gly Pro Arg Glu His Val Val Arg Lys Thr
    130                 135                 140

gag gac gac ggc ttc gcg gac acc ggg ctc ggc gcc ctg ctc gac gct      480
Glu Asp Asp Gly Phe Ala Asp Thr Gly Leu Gly Ala Leu Leu Asp Ala
145                 150                 155                 160

gcg ggc gtg acc gaa ctg gcg gtg tgc ggg gtg ctc tcc gaa atg tgc      528
Ala Gly Val Thr Glu Leu Ala Val Cys Gly Val Leu Ser Glu Met Cys
                165                 170                 175

gtc gcc gcc acc gcg cgc acc gcc ctg gag ctg ggc cac cgc gtc gtc      576
Val Ala Ala Thr Ala Arg Thr Ala Leu Glu Leu Gly His Arg Val Val
            180                 185                 190

ctc ccg cac gac gcg cac gcc acc tac gac atc ccc gcc gcg ccc gac      624
Leu Pro His Asp Ala His Ala Thr Tyr Asp Ile Pro Ala Ala Pro Asp
        195                 200                 205

atc agc gac acc gtc ccg gcc gcg atg tcc tcc cgg gcc gcg gag tgg      672
Ile Ser Asp Thr Val Pro Ala Ala Met Ser Ser Arg Ala Ala Glu Trp
    210                 215                 220

gcc ctc ggc gac gag gtc gag atc gtc ccg cgc gcc gcc gcg gtc ccc      720
Ala Leu Gly Asp Glu Val Glu Ile Val Pro Arg Ala Ala Ala Val Pro
225                 230                 235                 240

ttc gtc gcc ccg ccg ctg gcg ccc gcc ccc gag gcc ccc gct gcc gcc      768
Phe Val Ala Pro Pro Leu Ala Pro Ala Pro Glu Ala Pro Ala Ala Ala
                245                 250                 255

gct gca ccc gcg gcc ggt acg ggg ctc agc cct gct ggt ccg ccg ccc      816
Ala Ala Pro Ala Ala Gly Thr Gly Leu Ser Pro Ala Gly Pro Pro Pro
            260                 265                 270

gct cca gcg cgc tga                                                  831
Ala Pro Ala Arg
        275


<210> SEQ ID NO 16
<211> LENGTH: 276
<212> TYPE: PRT
<213> ORGANISM: Streptomyces albulus

<400> SEQUENCE: 16

Met Ile Arg Pro Asp Arg Cys Pro Trp Gln Pro Cys Pro Ser Gly Arg
1               5                   10                  15

Tyr Leu Ser Arg Pro Ser Gly Arg Val Pro Arg Ser Thr Met Met Thr
            20                  25                  30

Pro Met Thr Ala Met Pro Ala Val Thr Ala Met Pro Pro Glu Thr Ala
        35                  40                  45

Ala Pro Pro Glu Thr Ala Ala Pro Ala Arg Pro Leu Arg Pro Val Gln
    50                  55                  60

Ala Leu Leu Val Val Asp Val Gln Thr Ala Phe Val Ser Gly Ala Glu
65                  70                  75                  80

Ala Val Pro Glu Ala Ala Arg Val Leu Asp Arg Thr Arg Gly Leu Leu
                85                  90                  95

Ala Arg Ala Arg Thr Ala Gly Ala Leu Val Val His Leu Gln Asn Asp
            100                 105                 110

Gly Ala Pro Gly Ala Val Asp Ala Pro His Thr Pro Gly Trp Glu Leu
        115                 120                 125

His Leu Pro Val Glu Pro Gly Pro Arg Glu His Val Val Arg Lys Thr
    130                 135                 140

Glu Asp Asp Gly Phe Ala Asp Thr Gly Leu Gly Ala Leu Leu Asp Ala
145                 150                 155                 160
```

```
Ala Gly Val Thr Glu Leu Ala Val Cys Gly Val Leu Ser Glu Met Cys
                165                 170                 175

Val Ala Ala Thr Ala Arg Thr Ala Leu Glu Leu Gly His Arg Val Val
            180                 185                 190

Leu Pro His Asp Ala His Ala Thr Tyr Asp Ile Pro Ala Ala Pro Asp
        195                 200                 205

Ile Ser Asp Thr Val Pro Ala Ala Met Ser Ser Arg Ala Ala Glu Trp
    210                 215                 220

Ala Leu Gly Asp Glu Val Glu Ile Val Pro Arg Ala Ala Ala Val Pro
225                 230                 235                 240

Phe Val Ala Pro Pro Leu Ala Pro Ala Pro Glu Ala Pro Ala Ala Ala
                245                 250                 255

Ala Ala Pro Ala Ala Gly Thr Gly Leu Ser Pro Ala Gly Pro Pro Pro
            260                 265                 270

Ala Pro Ala Arg
        275
```

<210> SEQ ID NO 17
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n represents g or c
<220> FEATURE:
<221> NAME/KEY: misc_feature
<222> LOCATION: (9)..(9)
<223> OTHER INFORMATION: n represents a or g
<220> FEATURE:
<221> NAME/KEY: misc_feature
<222> LOCATION: (12)..(12)
<223> OTHER INFORMATION: n represents g or c
<220> FEATURE:
<221> NAME/KEY: misc_feature
<222> LOCATION: (18)..(18)
<223> OTHER INFORMATION: n represents a or g
<220> FEATURE:
<221> NAME/KEY: misc_feature
<222> LOCATION: (20)..(20)
<223> OTHER INFORMATION: n represents g or c
<220> FEATURE:
<221> NAME/KEY: misc_feature
<222> LOCATION: (21)..(21)
<223> OTHER INFORMATION: n represents g or c
<220> FEATURE:
<221> NAME/KEY: misc_feature
<222> LOCATION: (24)..(24)
<223> OTHER INFORMATION: n represents g or c

<400> SEQUENCE: 17
gacgcngang cnatcgangn nctnga 26

<210> SEQ ID NO 18
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n represents c or t
<220> FEATURE:
<221> NAME/KEY: misc_feature
<222> LOCATION: (10)..(10)
<223> OTHER INFORMATION: n represents g or c

```
<220> FEATURE:
<221> NAME/KEY: misc_feature
<222> LOCATION: (13)..(13)
<223> OTHER INFORMATION: n represents g or c
<220> FEATURE:
<221> NAME/KEY: misc_feature
<222> LOCATION: (16)..(16)
<223> OTHER INFORMATION: n represents c or t
<220> FEATURE:
<221> NAME/KEY: misc_feature
<222> LOCATION: (19)..(19)
<223> OTHER INFORMATION: n represents g or c

<400> SEQUENCE: 18

gttstngttn gtnacntcna gcca                                              24


<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19

gggggatcca ccactcttga cgacacggct                                        30


<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20

accaagcttt caggggcagg gcatgctcat                                        30


<210> SEQ ID NO 21
<211> LENGTH: 33
<212> TYPE: DNA
<213> ORGANISM: Artificial Sequence
<220> FEATURE:
<223> OTHER INFORMATION: Primer

<400> SEQUENCE: 21

accaagctta atatgaccac tcttgacgac acg                                    33


<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22

aaactgcagt caggggcagg gcatgctcat                                        30


<210> SEQ ID NO 23
<211> LENGTH: 33
<212> TYPE: DNA
<213> ORGANISM: Artificial Sequence
<220> FEATURE:
<223> OTHER INFORMATION: Primer

<400> SEQUENCE: 23

accaagctta ccatgccccc cgagaccgcc gcg                                    33
```

-continued

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
aaactgcagt cagcgcgctg gagcgggcgg 30

<210> SEQ ID NO 25
<211> LENGTH: 978
<212> TYPE: DNA
<213> ORGANISM: Streptomyces albulus NBRC14147

<400> SEQUENCE: 25
ctcgaacccc ggtgcgcagc ggccgttgac ggtgacagcc tccacggtgg ccctcctcgc 60
gtcgtcgcgg tgcggtcgga tgccgcgccc cgccgcacgg aacgcccacg cacggaaccg 120
acgcgcgcac ggccggagca cctacggatg atccgcccgg atcgatgccc gtggcaacca 180
tgcccgtccg gccggtacct ttcccgcccg tccggccgag tgccgcgttc gacgatgatg 240
acccccatga ccgccatgcc cgccgtgacc gccatgcccc ccgagaccgc cgcgcccccc 300
gagaccgccg cgcccgcccg gccgctccgc cccgtacagg ccctcctcgt cgtcgacgtc 360
caaaccgcgt tcgtctccgg ggccgaggcg gtccccgagg cggcccgggt cctggaccgc 420
acccgtggcc tgctcgcccg cgcccgcacc gccggcgccc tcgtcgtcca cctccagaac 480
gacggcgcgc ccggcgccgt cgacgcaccg cacaccccg gctgggaact ccacctcccc 540
gtcgagcccg gcccccgcga gcacgtggtc cgcaagaccg aggacgacgg cttcgcggac 600
accgggctcg gcgccctgct cgacgctgcg ggcgtgaccg aactggcggt gtgcggggtg 660
ctctccgaaa tgtgcgtcgc cgccaccgcg cgcaccgccc tggagctggg ccaccgcgtc 720
gtcctcccgc acgacgcgca cgccacctac gacatccccg ccgcgcccga catcagcgac 780
accgtcccgg ccgcgatgtc ctcccgggcc gcggagtggg ccctcggcga cgaggtcgag 840
atcgtcccgc gcgccgccgc ggtccccttc gtcgccccgc cgctggcgcc cgcccccgag 900
gcccccgctg ccgccgctgc acccgcggcc ggtacggggc tcagccctgc tggtccgccg 960
cccgctccag cgcgctga 978

<210> SEQ ID NO 26
<211> LENGTH: 276
<212> TYPE: PRT
<213> ORGANISM: Streptomyces albulus NBRC14147

<400> SEQUENCE: 26

```
Met Ile Arg Pro Asp Arg Cys Pro Trp Gln Pro Cys Pro Ser Gly Arg
1               5                   10                  15

Tyr Leu Ser Arg Pro Ser Gly Arg Val Pro Arg Ser Thr Met Met Thr
            20                  25                  30

Pro Met Thr Ala Met Pro Ala Val Thr Ala Met Pro Pro Glu Thr Ala
        35                  40                  45

Ala Pro Pro Glu Thr Ala Ala Pro Ala Arg Pro Leu Arg Pro Val Gln
    50                  55                  60

Ala Leu Leu Val Val Asp Val Gln Thr Ala Phe Val Ser Gly Ala Glu
65                  70                  75                  80

Ala Val Pro Glu Ala Ala Arg Val Leu Asp Arg Thr Arg Gly Leu Leu
                85                  90                  95
```

-continued

```
Ala Arg Ala Arg Thr Ala Gly Ala Leu Val Val His Leu Gln Asn Asp
            100                 105                 110

Gly Ala Pro Gly Ala Val Asp Ala Pro His Thr Pro Gly Trp Glu Leu
        115                 120                 125

His Leu Pro Val Glu Pro Gly Pro Arg Glu His Val Val Arg Lys Thr
    130                 135                 140

Glu Asp Asp Gly Phe Ala Asp Thr Gly Leu Gly Ala Leu Leu Asp Ala
145                 150                 155                 160

Ala Gly Val Thr Glu Leu Ala Val Cys Gly Val Leu Ser Glu Met Cys
                165                 170                 175

Val Ala Ala Thr Ala Arg Thr Ala Leu Glu Leu Gly His Arg Val Val
            180                 185                 190

Leu Pro His Asp Ala His Ala Thr Tyr Asp Ile Pro Ala Ala Pro Asp
        195                 200                 205

Ile Ser Asp Thr Val Pro Ala Ala Met Ser Ser Arg Ala Ala Glu Trp
    210                 215                 220

Ala Leu Gly Asp Glu Val Glu Ile Val Pro Arg Ala Ala Ala Val Pro
225                 230                 235                 240

Phe Val Ala Pro Pro Leu Ala Pro Ala Pro Glu Ala Pro Ala Ala Ala
                245                 250                 255

Ala Ala Pro Ala Ala Gly Thr Gly Leu Ser Pro Ala Gly Pro Pro Pro
            260                 265                 270

Ala Pro Ala Arg
        275
```

LACTAM RING-OPENING ENZYME AND USE THEREOF

CROSS REFERENCE TO RELATED APPLICATIONS

This application claims priority under 35 U.S.C §119 to Japanese Patent Application No. 2006-050371 filed Feb. 27, 2006, which is herein incorporated by reference in its entirety.

BACKGROUND OF THE INVENTION

1. Field of the Invention

The invention relates to a novel lactam ring-opening enzyme, and to a use thereof. More specifically, the invention relates to a novel lactam ring-opening enzyme having the activity of opening the lactam ring of a streptothricin derivative, to a method for manufacturing a lactam ring-opened streptothricin derivative using this enzyme, and to an antimicrobial agent containing the lactam ring-opened streptothricin derivative and the like.

2. Related Art

Streptothricins (sometimes abbreviated as "ST," see FIG. 1) are broad-spectrum antibiotics first isolated from *Streptomyces lavendulae* in 1943 (Waksman, S. A., *J. Bacteriol.,* 46, 299-310 (1943)). All STs include a carbamoylated D-gulosamine to which is attached a β-lysine homopolymer (1 to 7 residues), and the unusual amino acid streptolidine in the amide form (streptolidine lactam). STs are potent inhibitors of protein biosynthesis in prokaryotic cells, and also strongly inhibit the growth of eukaryotic cells such as yeasts, fungi, protozoa, insects and plants. Consequently, they are used as effective selective agents for recombinant DNA work in some of these organisms. However, STs are not used therapeutically due to their nephrotoxicity.

Many ST resistance genes have already been identified in Tn1825, Tn1826 and other transposons isolated from ST-resistant bacteria (Partridge, S. R. & Hall, R. M., *J. Clin. Microbiol.,* 43, 4298-4300 (2005)), and transposons of this kind have also been isolated from clinically problematic pathogens such as Shiga toxin-producing *E. coli* (Singh, R et al., S., *J. Antimicrob. Chemother.,* 56, 216-219 (2005) and a *Shigella* strain (Peirano, G et al., *J. Antimicrob. Chemother.,* 55, 301-305 (2005). Bacterial resistance to antibiotics exhibiting protein biosynthesis inhibition activity (such as aminoglycosides) can result from three causes (Vakulenko, S. B. & Mobashery, S. (2003), Clin. Microbiol. Rev. 16, 430-450): (1) decreased antibiotic uptake and accumulation, (2) modification of 16S RNA or ribosomal proteins, and (3) enzymatic modification of the antibiotics. In the case of bacterial resistance to STs, however, so far the only known resistance mechanism is a common resistance mechanism in which the ST molecule is modified by monoacetylation (see FIG. 1) of the β-amino group (position 16) of the β-lysine. In fact, ST-resistance genes encoding N-acetyltransferase (NAT) have also been identified in ST-producers such as *Streptomyces lavendulae* (Horinouchi, S. et al., *J. Bacteriol.,* 169, 1929-1937 (1987)), *Streptomyces rochei* (Fernandez-Moreno, M. A., Vallin, C. & Malpartida, F., *J. Bacteriol.,* 179, 6929-6936 (1997)) and *Streptomyces noursei* (Krugel, H. et al, *Gene,* 62, 209-217 (1988); Grammel, N., et al., *Eur. J. Biochem.,* 269, 347-357 (2002)), and the roles played by these genes in self-resistance against their own STs are being investigated. On the basis of this resistance mechanism, and the fact that ST-D is more effective than ST-F as an antibiotic against many bacteria, it has been shown that the β-lysine moiety plays a crucial role in antibiotic activity. On the other hand, the groups of Inamori (Inamori, Y. et al., *Chem. Pharm. Bull.* (Tokyo), 36, 1577-80 (1988)) and Taniyama (Taniyama, H., Sawada, Y. & Kitagawa, T., *J. Antibiot.* (Tokyo), 24, 662-666 (1971)) have independently reported that ST-F-acid (FIG. 1; racenomycin-A-acid in their work), which was chemically synthesized from ST-F, did not exhibit antibiotic activity against bacteria, fungi and plants. These results confirmed that the streptolidine lactam is also indispensable for antibiotic activity. However, the antibiotic activity of ST-D-acid has not been tested.

Under these circumstances, there is demand for an enzyme capable of reducing the antibiotic activity (that is, toxicity) of streptothricin with respect to eukaryotic cells without sacrificing antibiotic activity with respect to prokaryotic cells, as well as a streptothricin derivative having reduced toxicity with respect to eukaryotic cells while retaining antibiotic activity with respect to prokaryotic cells, and a method for manufacturing this streptothricin derivative.

In an effort to solve the above-described problems, it has been discovered that a protein having the amino acid sequence of SEQ ID NO: 2, 4, 6, 8, 10, 12, 14 or 16 has the activity of opening the lactam ring of streptothricin. It has also been discovered that the lactam ring-opened streptothricin D derivative (ST-D-acid) obtained with this enzyme has reduced toxicity with respect to eukaryotic cells while retaining antibiotic activity with respect to prokaryotic cells.

SUMMARY OF THE INVENTION

The invention includes:

(1) A polynucleotide according to any of (a) to (f) below:

(a) a polynucleotide containing a polynucleotide including a nucleotide sequence according to SEQ ID NO: 1, 3, 5, 7, 9, 11, 13 or 15;

(b) a polynucleotide containing a polynucleotide coding for a protein including an amino acid sequence according to SEQ ID NO: 2, 4, 6, 8, 10, 12, 14 or 16;

(c) a polynucleotide containing a polynucleotide coding for a protein including an amino acid sequence according to SEQ ID NO: 2, 4, 6, 8, 10, 12, 14 or 16 with one or a plurality of amino acids deleted, substituted, inserted and/or added and having lactam ring-opening activity;

(d) a polynucleotide containing a polynucleotide coding for a protein having an amino acid sequence with 60% or more identity with an amino acid sequence according to SEQ ID NO: 2, 4, 6, 8, 10, 12, 14 or 16, and having lactam ring-opening activity;

(e) a polynucleotide containing a polynucleotide that hybridizes under stringent conditions with a polynucleotide including a nucleotide sequence complementary to a nucleotide sequence according to SEQ ID NO: 1, 3, 5, 7, 9, 11, 13 or 15, and that codes for a protein having lactam ring-opening activity; and (f) a polynucleotide containing a polynucleotide that hybridizes under stringent conditions with a polynucleotide including a nucleotide sequence complementary to a nucleotide sequence of a polynucleotide coding for a protein including an amino acid sequence according to SEQ ID NO: 2, 4, 6, 8, 10, 12, 14 or 16, and that codes for a protein having lactam ring-opening activity, (2) The polynucleotide according to (1) above which is any of (g) to (i) below:

(g) a polynucleotide containing a polynucleotide coding for a protein that includes an amino acid sequence according to SEQ ID NO: 2, 4, 6, 8, 10, 12, 14 or 16 or an amino acid sequence according to SEQ ID NO: 2, 4, 6, 8, 10, 12, 14 or 16 with 1 to 10 amino acids deleted, substituted, inserted and/or added, and that has lactam ring-opening activity;

(h) a polynucleotide containing a polynucleotide coding for a protein that has an amino acid sequence having 90% or more identity with an amino acid sequence according to SEQ ID NO: 2, 4, 6, 8, 10, 12, 14 or 16, and that has lactam ring-opening activity; and (i) a polynucleotide containing a polynucleotide that hybridizes under very stringent conditions with a polynucleotide including a nucleotide sequence according to SEQ ID NO: 1, 3, 5, 7, 9, 11, 13 or 15 or a polynucleotide including a nucleotide sequence complementary to a nucleotide sequence of SEQ ID NO: 1, 3, 5, 7, 9, 11, 13 or 15, and that codes for a protein having lactam ring-opening activity, (3) The polynucleotide according to (1) above, containing a polynucleotide including the nucleotide sequence of SEQ ID NO: 1, (4) The polynucleotide according to (1) above, containing a polynucleotide coding for a protein including the amino acid sequence of SEQ ID NO: 2, (5) The polynucleotide according to any of (1) to (4) above that is DNA, (6) A protein coded for by the polynucleotide according to any of (1) to (5) above, (7) The protein according to (6) above, including an amino acid sequence according to SEQ ID NO: 2, 4, 6, 8, 10, 12, 14 or 16, (8) The protein according to (7) above, including an amino acid sequence according to SEQ ID NO: 2, (9) A recombinant vector containing the polynucleotide according to any of (1) to (5) above,

(10) A transformant having the recombinant vector according to (9) introduced therein,

(11) A method for manufacturing the protein according to (6) above, including a step of culturing the transformant according to (10) above to produce the protein according to (6) above,

(12) A method for manufacturing a lactam ring-opened streptothricin derivative or salt thereof, including a step of using the protein according to (6) above to open the lactam ring,

(13) The manufacturing method according to (12) above, wherein the lactam ring-opened streptothricin derivative is a compound represented by Formula (I):

(I)

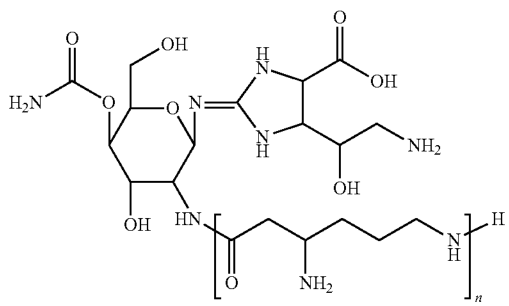

(wherein n is an integer between 1 and 7),

(14) The manufacturing method according to (13) above, wherein the compound represented by Formula (I) is a compound represented by Formula (II), (II)

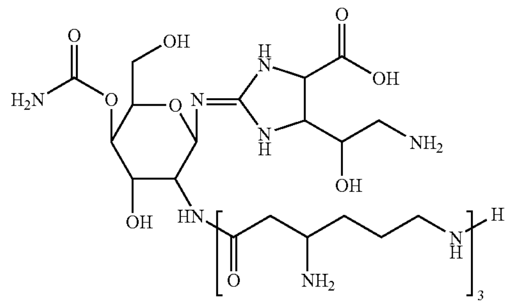

(15) An antimicrobial composition including a compound represented by Formula (II)

(II)

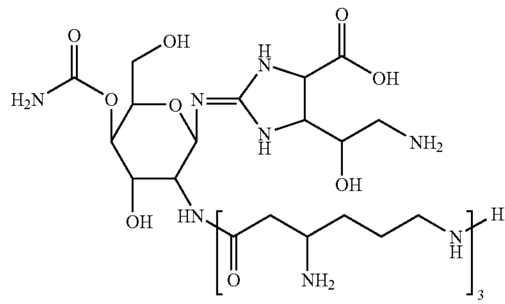

or a salt thereof, and a carrier.

Due to the opening of the lactam ring of streptothricin, the protein of the invention can reduce the antibiotic activity (that is, toxicity) of streptothricin with respect to eukaryotic cells without sacrificing antibiotic activity with respect to prokaryotic cells, it can be used to manufacture streptothricin derivatives that have potential for clinical development and as lead compounds for drug discovery.

Moreover, because the polynucleotide of the invention can confer streptothricin resistance on eukaryotic cells (such as yeasts), it can be used favorably in recombinant DNA technology as an antibiotic resistance marker gene.

Additionally, because ST-D-acid has reduced antibiotic activity (that is, toxicity) with respect to eukaryotic cells while retaining antibiotic activity with respect to prokaryotic cells, it can be used as an antimicrobial agent or composition with potential for clinical development, or as a lead compound in the discovery of such antimicrobial agents or compositions.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings

FIG. 2 illustrates a diagram of a cloned 2.9 kb fragment involved in ST resistance and an ORF estimated by nucleotide sequencing (the DNA sequence is listing in SEQ. ID NO: 25, the corresponding amino acid sequence is listed in SEQ ID NO: 26). The diagonal box illustrates a DNA fragment subcloned to a pWHM3 plasmid. The nucleotide sequence of the sttH gene starts at the $8^{th}$ position (SEQ ID NO.: 1). A possible sttH gene initiation codon ($1^{st}$-$8^{th}$ positions) is enclosed in a gray box. The sequence of DNA coding for rSttH begins at the $7^{th}$ position (SEQ ID NO.: 3), $6^{th}$ position (SEQ ID NO.: 5), $5^{th}$ position (SEQ ID NO.: 7), $4^{th}$ position (SEQ ID NO.: 9), $3^{rd}$ position (SEQ ID NO.: 11), $2^{nd}$ position (SEQ ID NO.: 13), and $1^{st}$ position (SEQ ID NO.: 15). The PCR primers used in this study are indicated with arrows;

" and FIG. 4 illustrates the results of ESI-MS/MS analysis of ST-F and a substance (ST-F-acid) produced from ST-F by the action of rSttH. The ESI-MS and MS/MS spectra of ST-F dissolved in 0.2% formic acid+50% acetonitrile (A) and ST-F-acid (B) are shown.

SEQUENCE TABLE FREE TEXT

Figure 1:
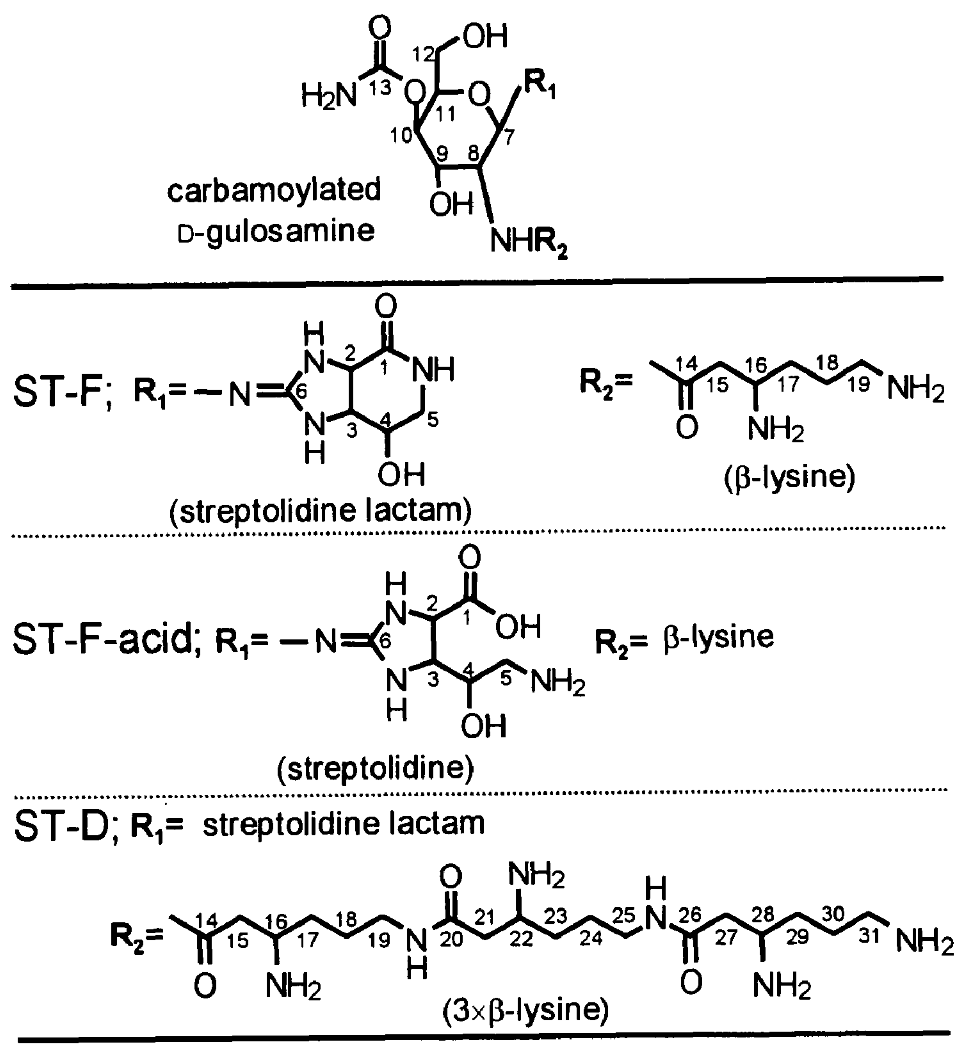
FIG. 1 illustrates the chemical structure of streptothricin (ST)

SEQ ID NO: 1 shows the nucleotide sequence of the sttH gene (starting at $8^{th}$ position in FIG. 2).

SEQ ID NO: 2 shows the amino acid sequence of the SttH protein coded for by the sttH gene including the nucleotide sequence of SEQ ID NO: 1.

SEQ ID NO: 3 shows the nucleotide sequence of DNA coding for rSttH, beginning at the $7^{th}$ position in FIG. 2.

SEQ ID NO: 4 shows the amino acid sequence of rSttH coded for by DNA including the nucleotide sequence of SEQ ID NO: 3.

SEQ ID NO: 5 shows the nucleotide sequence of DNA coding for rSttH beginning at the $6^{th}$ position in FIG. 2.

SEQ ID NO: 6 shows the amino acid sequence of rSttH coded for by DNA including the nucleotide sequence of SEQ ID NO: 5.

SEQ ID NO: 7 shows the nucleotide sequence of DNA coding for rSttH beginning at the $5^{th}$ position in FIG. 2.

SEQ ID NO: 8 shows the amino acid sequence of rSttH coded for by DNA including the nucleotide sequence of SEQ ID NO: 7.

SEQ ID NO: 9 shows the nucleotide sequence of DNA coding for rSttH beginning at the $4^{th}$ position in FIG. 2.

SEQ ID NO: 10 shows the amino acid sequence of rSttH coded for by DNA including the nucleotide sequence of SEQ ID NO: 9.

SEQ ID NO: 11 shows the nucleotide sequence of DNA coding for rSttH beginning at the $3^{rd}$ position in FIG. 2.

SEQ ID NO: 12 shows the amino acid sequence of rSttH coded for by DNA including the nucleotide sequence of SEQ ID NO: 11.

SEQ ID NO: 13 shows the nucleotide sequence of DNA coding for rSttH beginning at the $2^{nd}$ position in FIG. 2.

SEQ ID NO: 14 shows the amino acid sequence of rSttH coded for by DNA including the nucleotide sequence of SEQ ID NO: 13.

SEQ ID NO: 15 shows the nucleotide sequence of DNA coding for rSttH beginning at the $1^{st}$ position in FIG. 2.

SEQ ID NO: 16 shows the amino acid sequence of rSttH coded for by DNA including the nucleotide sequence of SEQ ID NO: 15.

SEQ ID NO: 17 shows the nucleotide sequence of a primer used in "Materials and Methods" (3) in the aforementioned examples.

SEQ ID NO: 18 shows the nucleotide sequence of a primer used in "Materials and Methods" (3) in the aforementioned examples.

SEQ ID NO: 19 shows the nucleotide sequence of a primer used in "Materials and Methods" (9) in the aforementioned examples.

SEQ ID NO: 20 shows the nucleotide sequence of a primer used in "Materials and Methods" (9) in the aforementioned examples.

SEQ ID NO: 21 shows the nucleotide sequence of a primer used in "Materials and Methods" (9) in the aforementioned examples.

SEQ ID NO: 22 shows the nucleotide sequence of a primer used in "Materials and Methods" (9) in the aforementioned examples.

SEQ ID NO: 23 shows the nucleotide sequence of a primer used in "Materials and Methods" (9) in the aforementioned examples.

SEQ ID NO: 24 shows the nucleotide sequence of a primer used in "Materials and Methods" (9) in the aforementioned examples.

SEQ ID NO: 25 shows the nucleotide sequence of the cloned fragment involved in ST resistance shown in FIG. 2.

SEQ ID NO: 26 shows the amino acid sequence corresponding to the nucleotide sequence of SEQ ID NO: 25.

DETAILED DESCRIPTION OF THE INVENTION

A gene (sttH) conferring ST resistance by a new mechanism from *Streptomyces albulus* NBRC14147, which is believed not to produce streptothricin (ST), has been isolated. In vivo and in vitro analysis of SttH demonstrated that this enzyme catalyzes the hydrolysis of the amide bond of streptolidine lactam, thereby conferring ST resistance. Interestingly, the selective toxicity of ST-D possessing 3×β-lysine residues was switched from broad-spectrum to bacterial-specific by the hydrolysis of the streptolidine lactam, although the ST-F (1×β-lysine residue) was detoxified by SttH in both prokaryotes and eukaryotes (yeasts). STs have never been clinically developed due to their toxicity in mammals. However, in this study it was shown that lactam ring-opened ST-D (also called ST-D-acid) produced by hydrolysis with SttH still retains strong antibacterial activity while having reduced toxicity with respect to eukaryotic cells, suggesting that ST-D-acid has potential for clinical development or as a new lead compound for drug discovery. Besides, the use of ST-D in combination with the sttH gene could be a powerful tool in recombinant DNA work in eukaryotic cells including yeasts.

Based on these findings, the invention provides a protein (novel lactam ring-opening enzyme) capable of reducing the antibiotic activity (that is, toxicity) of streptothricin (ST) with respect to eukaryotic cells without sacrificing antibiotic activity with respect to prokaryotic cells, as well as a polynucleotide coding for this protein, a vector containing this polynucleotide, a transformant having this vector or polynucleotide introduced therein, a method for manufacturing this protein using this transformant, a method for using this protein to manufacture a streptothricin derivative having reduced toxicity with respect to eukaryotic cells while retaining antibiotic activity (that is, toxicity) with respect to prokaryotic cells, an antimicrobial agent or composition comprising ST-D-acid and the like.

1. Polynucleotide of the Invention

In this Specification, a polynucleotide containing a polynucleotide including the nucleotide sequence according to SEQ ID NO: 1 is called an "sttH gene."

First, the invention provides (a) a polynucleotide (specifically DNA, hereunder sometimes called "DNA") containing a polynucleotide including a nucleotide sequence according to SEQ ID NO: 1, 3, 5, 7, 9, 11, 13 or 15; and (b) a polynucleotide containing a polynucleotide coding for a protein including an amino acid sequence according to SEQ ID NO: 2, 4, 6, 8, 10, 12, 14 or 16. The subject DNA of the invention is not limited to DNA coding to the novel lactam ring-opening enzyme derived from *Streptomyces albulus* NBRC14147 which is described above, but also includes other DNA coding for proteins that are functionally equivalent to this protein. A functionally equivalent protein is for example (c) a protein including an amino acid sequence according to SEQ ID NO: 2, 4, 6, 8, 10, 12, 14 or 16 with one or a plurality of amino acids deleted, substituted, inserted and/or added and having lactam ring-opening activity. An example of such a protein is a protein including an amino acid sequence according to SEQ ID NO: 2, 4, 6, 8, 10, 12, 14 or 16 with for example 1 to 100, 1 to 70, 1 to 50, 1 to 30, 1 to 15, 1 to 10, 1 to 9, to 8, 1 to 7, 1 to 6 (1 to a few), 1 to 5, 1 to 4, 1 to 3, 1 to 2 or 1 amino acid residues deleted, substituted, inserted and/or added, and having lactam ring-opening activity. In general, the number of amino acid residues that are deleted, substituted, inserted and/or added is preferably as small as possible. An example of such a protein is (d) a protein having approximately 80% or more, approximately 85% or more, approximately 88% or more, approximately 90% or more, approximately 92% or more, approximately 95% or more, approximately 97% or more, approximately 98% or more, approximately 99% or more, approximately 99.3% or more, approximately 99.5% or more, approximately 99.7% or more, approximately 99.8% or more, or approximately 99.9% or more identity with an amino acid sequence according to SEQ ID NO: 2, 4, 6, 8, 10, 12, 14 or 16, and having lactam ring-opening activity. In general, a greater percentage of identity is better. Identity of amino acid sequences or nucleotide sequences can be determined using an analytic program such as BLAST (see, e.g., Altzshul, S. F. et al., *J. Mol. Biol.,* 215, 403 (1990), etc.) or FASTA (see Pearson, W. R., *Methods in Enzymology,* 183, 63 (1990), etc.). BLAST or FASTA can be used according to the default parameters of the program. Lactam ring-opening activity can be measured by ordinary methods or analogous methods, such as the methods described in the examples below. In the invention, lactam ring-opening activity is specifically the activity of opening the lactam ring of streptothricin, and more specifically the activity of opening the streptolidine lactam ring of streptothricin. Lactam ring-opening is specifically accomplished by hydrolysis.

The invention also encompasses (e) a polynucleotide containing a polynucleotide that hybridizes under stringent conditions with a polynucleotide including a nucleotide sequence complementary to a nucleotide sequence according to SEQ ID NO: 1, 3, 5, 7, 9, 11, 13 or 15, and that codes for a protein having lactam ring-opening activity; and (f) a polynucleotide containing a polynucleotide that hybridizes under stringent conditions with a polynucleotide including a nucleotide sequence complementary to the nucleotide sequence of a polynucleotide coding for a protein including an amino acid sequence according to SEQ ID NO: 2, 4, 6, 8, 10, 12, 14 or 16, and that codes for a protein having lactam ring-opening activity.

A "polynucleotide (DNA) that hybridizes under stringent conditions" means DNA obtained by colony hybridization, plaque hybridization, Southern hybridization or the like using as the probe all or part of DNA including a nucleotide sequence complementary to a nucleotide sequence according to SEQ ID NO: 1, 3, 5, 7, 9, 11, 13 or 15 or all or part of DNA coding for an amino acid sequence according to SEQ ID NO: 2, 4, 6, 8, 10, 12, 14 or 16. Specifically, it may be a polynucleotide that is identified by first performing hybridization at approximately 65° C. with approximately 0.7 to approximately 1.0 mol/L of NaCl using a filter having fixed thereon colony- or plaque-derived DNA, and then washing the filter at approximately 65° C. with an approximately 0.1 to 2×SSC (Saline-sodium citrate) solution (a 1×SSC solution is composed of approximately 150 mmol/L sodium chloride and approximately 15 mmol/L sodium citrate).

Hybridization can be accomplished in accordance with the methods described in such experimental manuals as Sambrook, J. et al., MOLECULAR CLONING: A LABORATORY MANUAL, THIRD EDITION, Cold Spring Harbor Laboratory Press (2001) (hereafter "Molecular Cloning 3$^{rd}$ Ed."), Ausbel, F. M. et al., CURRENT PROTOCOLS IN MOLECULAR BIOLOGY, SUPPLEMENT 1-38, John Wiley and Sons (1987 to 1997) and Glover, D. M. and Hames, B. D., DNA CLONING 1: CORE TECHNIQUES, A PRACTICAL APPROACH, SECOND EDITION, Oxford University Press (1995).

In the Specification, "stringent conditions" may be either less stringent conditions, moderately stringent conditions or very stringent conditions. "Less stringent conditions" are, for example, conditions of 5×SSC, 5× Denhart's solution, 0.5% SDS, 50% formamide, 32° C. "Moderately stringent conditions" are, for example, conditions of 5×SSC, 5× Denhart's solution, 0.5% SDS, 50% formamide, 42° C. "Very stringent conditions" are, for example, conditions of 5×SSC, 5× Denhart's solution, 0.5% SDS, 50% formamide, 50° C. The more stringent the conditions, the greater the homology required for double strand formation. Specifically, it can be expected that highly homologous DNA will be obtained more efficiently the higher the temperature under these conditions. However, the stringency of hybridization is affected by multiple factors including temperature, probe concentration, probe length, ion strength, time, salt concentration and the like, and the same level of stringency can be achieved by a person skilled in the art by an appropriate selection of these factors.

When a commercial kit is used for hybridization, Alkphos Direct Labelling Reagents (Amersham Pharmacia) can be used for example. In this case, hybridization with the labeled probe can be accomplished overnight in accordance with the attached protocols, after which the membrane can be washed at 55° C. with a primary washing buffer of approximately 0.1% (w/v) SDS, and the hybridized DNA can then be detected.

Other hybridizable DNA includes DNA having approximately 80% or more, approximately 85% or more, approximately 88% or more, approximately 90% or more, approximately 92% or more, approximately 95% or more, approximately 97% or more, approximately 98% or more, approximately 99% or more, approximately 99.3% or more, approximately 99.5% or more, approximately 99.7% or more, approximately 99.8% or more, or approximately 99.9% or more identity with DNA coding for an amino acid sequence according to SEQ ID NO: 2, 4, 6, 8, 10, 12, 14 or 16 as calculated using an analysis program such as FASTA or BLAST according to the default parameters.

A polynucleotide coding for a protein having a particular amino acid sequence with one or a plurality of amino acids deleted, substituted, inserted and/or added can be obtained by a site-directed mutagenesis method (see, e.g., Gotoh, T. et al., *Gene* 152, 271-275 (1995); Zoller, M. J. and Smith, M.,

*Methods Enzymol.,* 100, 468-500 (1983); Kramer, W. et al., *Nucleic Acids Res.,* 12, 9441-9456 (1984); Kramer, W. and Fritz, H. J., *Methods Enzymol.,* 154, 350-367 (1987); Kunkel, T. A., *Proc. Natl. Acad. Sci. USA,* 82, 488-492 (1985); Kunkel, *Methods Enzymol.,* 85, 2763-2766 (1988)), or by a method using amber mutation (e.g., the Gapped duplex method, see *Nucleic Acids Res.,* 12, 9441-9456 (1984) or the like.

A mutation can also be introduced into a polynucleotide by PCR (see, e.g., Ho, S. N. et al., *Gene,* 77, 51 (1989), etc.) using a pair of primers each having at the 5' end a sequence with the target mutation (deletion, addition, substitution and/or insertion) introduced therein.

One kind of deletion mutant is a polynucleotide coding for a partial fragment of a protein, and this can be obtained by PCR with the polynucleotide coding for the protein as the template, using as primers an oligonucleotide having a sequence matching the nucleotide sequence of the 5' end and an oligonucleotide having a sequence complementary to the nucleotide sequence of the 3' end of the region coding for the desired partial fragment in the polynucleotide coding for the protein.

Specific examples of the polynucleotide of the invention include the polynucleotides described under (a) to (f) above. In the invention, (g) a polynucleotide containing a polynucleotide coding for a protein that includes an amino acid sequence according to SEQ ID NO: 2, 4, 6, 8, 10, 12, 14 or 16 or an amino acid sequence according to SEQ ID NO: 2, 4, 6, 8, 10, 12, 14 or 16 with 1 to 10 amino acids deleted, substituted, inserted and/or added, and that has lactam ring-opening activity, (h) a polynucleotide containing a polynucleotide coding for a protein that has an amino acid sequence having 90% or more identity with an amino acid sequence according to SEQ ID NO: 2, 4, 6, 8, 10, 12, 14 or 16, and that has lactam ring-opening activity, and (i) a polynucleotide containing a polynucleotide that hybridizes under very stringent conditions with a polynucleotide including a nucleotide sequence according to SEQ ID NO: 1, 3, 5, 7, 9, 11, 13 or 15 or a polynucleotide including a nucleotide sequence complementary to the nucleotide sequence of SEQ ID NO: 1, 3, 5, 7, 9, 11, 13 or 15, and that codes for a protein having lactam ring-opening activity are preferred as the polynucleotide, and a polynucleotide containing a polynucleotide coding for a protein having an amino acid sequence according to SEQ ID NO: 2, 4, 6, 8, 10, 12, 14 or 16 and a polynucleotide containing a polynucleotide including a nucleotide sequence according to SEQ ID NO: 1, 3, 5, 7, 9, 11, 13 or 15 are especially preferred, and a polynucleotide containing a polynucleotide coding for a protein having the amino acid sequence according to SEQ ID NO: 2 and a polynucleotide containing a polynucleotide including the nucleotide sequence according to SEQ ID NO: 1 are especially desirable from the standpoint of the lactam ring-opening activity of the protein coded thereby.

2. Protein of the Invention

The invention provides a protein coded for by the aforementioned polynucleotide of the invention. More specifically, this is a protein coded for by any of the polynucleotides (a) to (i) above, and preferably a protein that includes an amino acid sequence according to SEQ ID NO: 2, 4, 6, 8, 10, 12, 14 or 16 or a protein that includes an amino acid sequence according to SEQ ID NO: 2, 4, 6, 8, 10, 12, 14 or 16 with one or a plurality of amino acids deleted, substituted, inserted and/or added and that has lactam ring-opening activity, and more preferably a protein that includes an amino acid sequence according to SEQ ID NO: 2, 4, 6, 8, 10, 12, 14 or 16. Of these, a protein including the amino acid sequence according to SEQ ID NO: 2 is preferred from the standpoint of lactam ring-opening activity.

A protein that includes an amino acid sequence according to SEQ ID NO: 2, 4, 6, 8, 10, 12, 14 or 16 with one or a plurality of amino acids deleted, substituted, inserted and/or added and that has lactam ring-opening activity may be a protein that includes an amino acid sequence according to SEQ ID NO: 2, 4, 6, 8, 10, 12, 14 or 16 with amino acid residues deleted, substituted, inserted and/or added in numbers such as those described above, and that has lactam ring-opening activity. An example of such a protein is a protein that has an amino acid sequence having homology such as that described above with an amino acid sequence according to SEQ ID NO: 2, 4, 6, 8, 10, 12, 14 or 16, and that has lactam ring-opening activity. Such proteins can be obtained by site-directed mutagenesis as described in Molecular Cloning 3$^{rd}$ Ed., Current Protocols in Molecular Biology, *Nuc. Acids Res.,* 10, 6487 (1982), *Proc. Natl. Acad. Sci. USA,* 79, 6409 (1982), *Gene,* 34, 315 (1985); Nuc. Acids Res., 13, 4431 (1985), *Proc. Natl. Acad. Sci. USA,* 82, 488 (1985) and the like.

For one or more amino acid residues to be deleted, substituted, inserted and/or added in the amino acid sequence of the protein of the invention means that there are one or a plurality of amino acid residue deletions, substitutions, insertion and/or additions at any one or a plurality of positions in the same amino acid sequence, and deletions, substitutions, insertions and substitutions may each occur in two or more positions simultaneously.

Examples of mutually substitutable amino acid residues are given here. Amino acid residues belonging to the same group are mutually substitutable. These are: leucine, isoleucine, norleucine, valine, norvaline, alanine, 2-aminobutyric acid, methionine, o-methylserine, t-butylglycine, t-butylalanine and cyclohexylalanine in the A group; aspartic acid, glutamic acid, isoaspartic acid, isoglutamic acid, 2-aminoadipic acid and 2-aminosuberic acid in the B group; asparagine and glutamine in the C group; lysine, arginine, omithine, 2,4-diaminobutyric acid and 2,3-diaminopropionic acid in the D group; proline, 3-hydroxyproline and 4-hydroxyproline in the E group; serine, threonine and homoserine in the F group; and phenylalanine and tyrosine in the G group.

The protein of the invention can also be manufactured by a chemical synthesis method such as the Fmoc (fluorenyl methyloxycarbonyl) method or tBoc (t-butyloxycarbonyl) method. It can also be synthesized using a peptide synthesizer made by Advanced ChemTech, PerkinElmer, Pharmacia, Protein Technologies Incorporated, Synthecell/Vega, Perceptive, Shimazu Manufacturing or the like.

3. Recombinant Vector and Transformant of the Invention

The invention also provides a recombinant vector and transformant containing the aforementioned polynucleotide (DNA) of the invention. The recombinant vector of the invention contains a polynucleotide (DNA) according to any of (a) to (i) above. The transformant of the invention has the recombinant vector of the invention inserted therein in such a way that polynucleotide (DNA) of the invention can be expressed.

(1) Preparation of Recombinant Vector

The recombinant vector of the invention is obtained by linking (inserting) the polynucleotide (DNA) of the invention into a suitable vector. More specifically, it can be obtained by cleaving purified DNA with a suitable restriction enzyme, and then inserting it into a restriction enzyme site or multicloning site of a suitable vector to thereby link the DNA to the vector. The vector into which the polynucleotide of the invention is inserted may be any capable of replicating in a host, without limitations, and examples include plasmids, bacteriophages and animal viruses. Examples of plasmids include *E. coli*-derived plasmids (such as pBR322, pBR325, pUC118 and pUC119), *B. subtilis*-derived plasmids (such as pUB110 and pTP5), yeast-derived plasmids (such as YEp13, YEp24 and YCp50) and the like. Examples of bacteriophages include λ-phages and the like. Examples of animal viruses include retroviruses, vaccinia viruses, insect viruses (such as baculoviruses) and the like.

The polynucleotide of the invention is normally linked expressably downstream from a promoter of a suitable vector. When the host to be transformed is an animal cell, the promoter is preferably an SV40-derived promoter, retrovirus promoter, metallothionein promoter, heat shock promoter, cytomegalovirus promoter, SRα promoter or the like. When the host is an *Escherichia*, it is preferably a Trp promoter, T7 promoter, lac promoter, recA promoter, λPL promoter, 1pp promoter or the like. When the host is a *Bacillus*, it is preferably a SPO1 promoter, SPO2 promoter, penP promoter or the like. When the host is a yeast, it is preferably a PHO5 promoter, PGK promoter, GAP promoter, ADH1 promoter, GAL promoter or the like. When the host is an insect cell, it is preferably a polyhedrin promoter, P10 promoter or the like.

In addition, the recombinant vector of the invention may also contain an enhancer, splicing signal, poly-A addition signal, ribosome binding sequence (SD sequence), selection marker and the like as desired. Examples of selection markers include dihydrofolic acid reductase genes, ampicillin resistance genes, neomycin resistance genes and the like.

(2) Preparation of Transformant

The recombinant vector containing the polynucleotide of the invention (that is, DNA coding for the protein of the invention) obtained in this way can be inserted into a suitable host to prepare a transformant. The host is not particularly limited as long as it can express the DNA of the invention, and examples include *Escherichia* species, *Bacillus* species, *Pseudomonas* species and *Rhizobium* species, yeasts, animal cells, insect cells and the like. Examples of *Escherichia* species include *Escherichia coli* and the like. Examples of *Bacillus* species include *Bacillus subtilis* and the like. Examples of *Pseudomonas* species include *Pseudomonas putida* and the like. Examples of *Rhizobium* species include *Rhizobium meliloti* and the like. Examples of yeasts include *Saccharomyces cerevisiae, Schizosaccharomyces pombe* and the like. Examples of animal cells include COS cells, CHO cells and the like. Examples of insect cells include Sf9, Sf21 and the like.

Insertion of the recombinant vector and transformation of the host may be accomplished by various ordinary methods. Examples of methods for inserting recombinant vectors into host cells include the calcium phosphate method (*Virology,* 52, 456-457 (1973)), lipofection (*Proc. Natl. Acad. Sci. USA,* 84, 7413 (1987)), electroporation (*EMBO J.,* 1, 841-845 (1982)) and the like. *Escherichia* species can be transformed for example by the methods described in *Proc. Natl. Acad. Sci. USA,* 69, 2110 (1972) and *Gene,* 17, 107 (1982). *Bacillus* species can be transformed for example by the methods described in *Molecular & General Genetics,* 168, 111 (1979). Yeasts can be transformed for example by the methods described in *Proc. Natl. Acad. Sci. USA,* 75, 1929 (1978). Animal cells can be transformed for example by the methods described in *Virology,* 52, 456 (1973). Insect cells can be transformed for example by the methods described in *Bio/Technology,* 6, 47-55 (1988). A transformant transformed by a recombinant vector containing DNA coding for the protein of the invention is obtained in this way.

4. Manufacture of Protein of the Invention

The invention also provides a method for manufacturing the protein of the invention that includes a step of culturing the aforementioned transformant so that it produces the protein of the invention. The protein of the invention can be manufactured by culturing this transformant under conditions which allow the transformant to express DNA coding for the protein of the invention so that the protein of the invention is thereby produced and accumulated, and then isolating and purifying the protein.

Culture of Transformant

The transformant of the invention can be cultured by normal methods for culturing hosts. As a result of this culture, the protein of the invention is produced by the transformant and accumulates either in the transformant or in the culture liquid.

The medium for culturing a transformant when the host is an *Escherichia* species or *Bacillus* species may be either natural or synthetic medium as long as it contains a carbon source, a nitrogen source, inorganic salts and the like required for the growth of the transformant so as to permit efficient growth of the transformant. A carbohydrate such as glucose, fructose, sucrose or starch, an organic acid such as acetic acid or propionic acid or an alcohol such as ethanol or propanol can be used as the carbon source. The nitrogen source may be ammonia, ammonium chloride, ammonium sulfate, ammonium acetate, ammonium phosphate or another ammonium salt of an inorganic or organic acid, a nitrogen-containing compound, or peptone, meat extract, corn steep liquor or the like. Potassium primary phosphate, potassium secondary phosphate, magnesium phosphate, magnesium sulfate, sodium chloride, ferrous sulfate, manganese sulfate, copper sulfate, calcium carbonate and the like can be used as inorganic salts. An antibiotic such as ampicillin or tetracycline can be added to the medium as necessary during culture. When culturing a transformant transformed with an expression vector using an inducible promoter as the promoter, an inducer can be added to the medium as necessary. For example, isopropyl-β-D-thiogalactopyranoside (IPTG) can be added to the medium when culturing a transformant transformed with an expression vector using a Lac promoter, while indoleacrylic acid (IAA) can be added to the medium when culturing a transformant transformed with an expression vector using a trp promoter.

When the host is an *Escherichia* species, it is normally cultured for approximately 3 to approximately 24 hours at approximately 15° C. to approximately 43° C., with aeration and agitation. When the host is a *Bacillus* species, it is normally cultured for approximately 6 to approximately 24 hours at approximately 30° C. to approximately 40° C., with aeration and agitation as necessary.

The medium for culturing the transformant when the host is a yeast may be Burkholder's minimum medium (*Proc. Natl. Acad. Sci. USA,* 77, 4505 (1980)) or SD medium containing approximately 0.5% casamino acids (*Proc. Natl. Acad. Sci. USA,* 81, 5330 (1984)) for example. The medium is preferably adjusted to a pH of approximately 5 to approximately 8. Culture is normally performed for approximately 24 to approximately 72 hours at approximately 20° C. to approximately 35° C., with aeration and agitation as necessary.

The medium for culturing the transformant when the host is an animal cell may be MEM medium containing approximately 5% to approximately 20% bovine fetal serum (*Science,* 122, 501 (1952)) or DMEM medium (*Virology,* 8, 396 (1959)) or the like for example. The pH is preferably approximately 6 to approximately 8. Culture is normally performed for approximately 15 to approximately 60 hours at approximately 30° C. to approximately 40° C., with aeration and agitation as necessary.

The medium for culturing the transformant when the host is an insect cell may be Grace's Insect Medium (*Nature,* 195, 788 (1962)) with additives such as inactivated 10% bovine serum added thereto as necessary. The medium is preferably adjusted to a pH of approximately 6.2 to approximately 6.4. Culture is normally performed for approximately 3 to approximately 5 days at approximately 27° C., with aeration and agitation as necessary.

Isolation and Purification of Protein of the Invention

The protein of the invention can be isolated and purified from this culture to obtain the protein of the invention. Culture here includes not only liquid culture, cultured bacterial cell bodies and cultured cells, but also crushed bacterial cell bodies and cultured cells. The protein of the invention can be isolated and purified by ordinary methods.

Specifically, when the protein of the invention accumulates in the cultured bacterial cell bodies or cultured cells, the bacterial cell bodies or cells may be crushed by ordinary methods (ultrasonic, lysozyme, freezing and thawing, etc.) after culture, and a raw extract of the protein of the invention can then be obtained by ordinary methods (centrifugation, filtration, etc.). When the protein of the invention accumulates in culture liquid, the bacterial cell bodies or cells can be separated from culture supernatant by ordinary methods (centrifugation, filtration, etc.) after completion of culture to obtain culture supernatant containing the protein of the invention.

The protein of the invention contained in the resulting extract or culture supernatant can be purified by ordinary methods of isolation and purification. Examples of isolation and purification methods include ammonium sulfate sedimentation, gel filtration chromatography, ion exchange chromatography, affinity chromatography, reverse-phase high-speed liquid chromatography, dialysis, ultrafiltration and the like, and these methods can be used either individually or in combination.

5. Manufacture of Lactam Ring-Opened Streptothricin Derivative

The invention provides a method for manufacturing a lactam ring-opened streptothricin derivative (also called ST-acid), comprising a step of lactam ring opening using the protein of the invention. Since the protein of the invention has the action of opening the lactam ring of streptothricin, a lactam ring-opened streptothricin derivative can be manufactured using the protein of the invention with streptothricin as the raw material.

The method for manufacturing a lactam ring-opened streptothricin derivative of the invention is explained with reference to Reaction Formula 1 below.

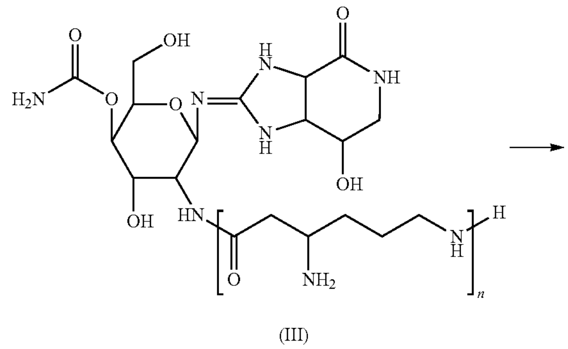

(III)

-continued

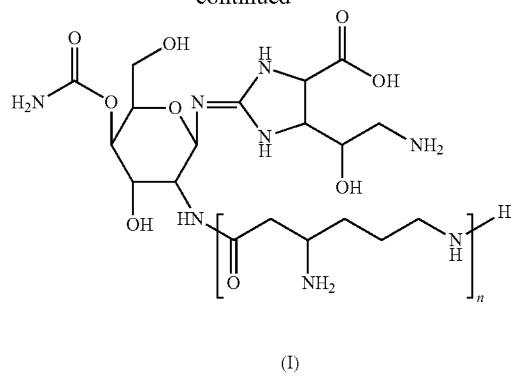

(I)

(wherein n represents an integer from 1 to 7).

Reaction Formula 1

Compound (III) is the raw material streptothricin, of which streptothricin X (n=7), A (n=6), B (n=5), C (n=4), D (n=3), E (n=2) and F (n=1) are known with differing lengths of the β-lysine chain. Streptothricin (that is, compound (III)) is commercially available, but can also be obtained by the methods described in the Documents (Doc. 1: Hamao Umezawa, Tomio Takeuchi and Eiji Kurosu, *J. Antibiot.,* 3, 232-235 (1949); Doc. 2: H. Taniyama, Y. Sawada & T. Kitagawa, *J. Antibiot.,* 24, 390-392 (1971); Doc. 3: S. Miyashiro, T. Ando, K. Hirayama, T. Kida, H. Shibai, A. Murai, T. Shiio & S. Udaka, *J. Antibiot.,* 36, 1638-1643 (1983); Doc. 4: T. Ando, S. Miyashiro, K. Hirayama, T. Kida, H. Shibai, A. Murai & S. Udaka, *J. Antibiot.,* 40, 1140-1145 (1987)).

The solvent used in the reaction may be a buffer such as sodium phosphate buffer, tris-hydrochloric acid buffer or the like. The pH of the reaction liquid is normally approximately 4.5 to approximately 8.0 or preferably approximately 6.0 to approximately 8.0 or more preferably approximately 6.5. The reaction temperature is normally 25° C. to approximately 65° C. or preferably approximately 35° C. to approximately 65° C. or more preferably approximately 45° C. The reaction time is normally approximately 30 minutes to approximately 2 hours, but can be set appropriately according to the reaction speed and the like.

The compound (I) produced by this reaction can be isolated and purified by commonly used methods such as reverse-phase high-speed liquid chromatography, gel filtration chromatography, extraction or the like.

When the resulting compound (I) is obtained in free form, it can be converted to a salt by ordinary methods. Conversely, when compound (I) is obtained as a salt, it can be converted to a free form or another salt by ordinary methods. A salt of a physiologically acceptable acid (inorganic acid, organic acid or the like) or base (alkaline metal or the like) is preferred as such a salt. Examples of salts of inorganic acids include salts of hydrochloric acid, sulfuric acid, phosphoric acid, hydrobromic acid and the like. Examples of salts of organic acids include salts of formic acid, acetic acid, trifluoracetic acid, citric acid, gluconic acid, tartaric acid, lactic acid, phthalic acid, fumaric acid, bromic acid, maleic acid, succinic acid, malic acid, methanesulfonic acid, p-toluenesulfonic acid, adipic acid, propionic acid, sorbic acid, benzoic acid, ascorbic acid and the like. Examples of salts of bases include metal salts, ammonium salts, salts of organic bases and the like. Examples of metal salts include salts of alkaline metals such as sodium, potassium and the like, salts of alkaline earth metals such as calcium, magnesium, barium and the like, and aluminum salts. Salts of organic bases includes trimethylamine, triethylamine, pyridine, picoline, 2,6-lutidine, ethanolamine, diethanolamine, triethanolamine, cyclohexylamine, dicyclohexylamine and N,N'-dibenzylethylenediamine salts and the like.

6. Antimicrobial Agent or Composition Including the Streptothricin Derivative of the Invention The invention also provides an antimicrobial agent or composition (sometimes simply referred to as “antimicrobial agent”) containing the streptothricin derivative of the invention, such as a lactam ring-opened streptothricin D derivative (ST-D-acid) or a salt thereof. A lactam ring-opened streptothricin D derivative (ST-D-acid) or salt thereof that can be manufactured by the manufacturing method described above has reduced antibiotic activity (that is, toxicity) with respect to eukaryotic cells, but retains antibiotic activity with respect to prokaryotic cells. Consequently, it can be used as an antimicrobial agent that can be safely used for eukaryotic organisms such as mammals (dogs, cats, guinea pigs, rats, mice, pigs, sheep, cows, etc.), birds, insects and the like.

From the standpoint of antibiotic activity with respect to prokaryotic cells, the lactam ring-opened streptothricin derivative used as the antimicrobial agent of the invention is preferably a lactam ring-opened streptothricin D derivative (ST-D-acid) or in other words the compound represented by Formula (II) above.

Examples of prokaryotic organisms towards which the lactam ring-opened streptothricin derivative of the invention exhibits antimicrobial activity include *E. coli* and other gram-negative bacteria, *Mycobacterium tuberculosis, Bacillus subtilis, Staphylococcus aureus* and other gram-positive bacteria and other pathogenic bacteria and the like.

Ordinary methods may be employed when using the lactam ring-opened streptothricin derivative or salt thereof of the invention as the aforementioned antimicrobial agent. Specifically, it can be used as follows for example. When using the lactam ring-opened streptothricin derivative or salt thereof of the invention as an antimicrobial agent, it can be administered orally, parenterally, intravenously, intraorally, rectally, vaginally, percutaneously, nasally or by inhalation either by itself or as a drug (e.g., pharmaceutical) composition, but preferably it is administered orally. Examples of drug compositions for oral administration include tablets (including sugar-coated tablets, coated tablets, press-coated tablets, sublingual tablets, intraoral adhering tablets and intraoral disintegrating tablets), pills, capsules (including hard capsules, soft capsules and microcapsules), powders, granules, grains, troches, liquids (including syrups, emulsions and suspensions), and the like. Examples of drug compositions for parenteral administration include injections, creams, ointments, suppositories and the like. These drug compositions can be compounded with carriers such as physiologically acceptable excipients, carriers and the like for example and manufactured by ordinary methods. Examples of physiologically acceptable excipients, carriers and the like include excipients, binders, disintegrants and lubricants used in solid preparations and solvents, solubilizers, suspending agents, buffers, viscosity improvers, emulsifiers and the like used in liquid preparations. Colorants, sweeteners, antioxidants and other pharmaceutical additives can also be added as necessary.

Examples of excipients include lactose, sucrose, D-mannitol, D-sorbitol, starch, alpha starch, dextrin, crystal cellulose (such as microcrystalline cellulose), low-substituted hydroxypropyl cellulose, carboxymethyl cellulose sodium, gum arabic, dextrin, pullulan, light anhydrous silicic acid, synthetic aluminum silicate, magnesium metasilicate aluminate and the like. Examples of binders include alpha starch, sucrose, gelatin, macrogol, gum arabic, methyl cellulose, carboxymethyl cellulose, carboxymethyl cellulose sodium, crystal cellulose, D-mannitol, trehalose, dextrin, pullulan, hydroxypropyl cellulose (HPC), hydroxypropyl methyl cellulose (HPMC), polyvinylpyrrolidone (PVP) and the like. Examples of disintegrants include lactose, sucrose, starch, carboxymethyl cellulose, carboxymethyl cellulose calcium, crosslinked polyvinylpyrrolidone, carmellose sodium, croscarmellose sodium, carboxymethyl starch sodium, light anhydrous silicic acid, low-substituted hydroxypropyl cellulose, cation exchange resin, partial alpha starch, corn starch and the like. Examples of lubricants include stearic acid, magnesium stearate, calcium stearate, talc, waxes, colloid silica, DL-leucine, sodium lauryl sulfate, magnesium lauryl sulfate, macrogol, Aerosil and the like.

Examples of solvents include injectable water, physiological saline, Ringer solution, alcohol, propylene glycol, polyethylene glycol, medium chain triglycerides (MCT), vegetable oils (such as safflower oil, sesame seed oil, corn oil, olive oil, cotton seed oil, soy lecithin, etc.) and the like. Examples of solubilizers include polyethylene glycol, polypropylene glycol, D-mannitol, trehalose, benzyl benzoate, ethanol, tris-aminomethane, cholesterol, triethanolamine, sodium carbonate, sodium citrate, sodium salicylate, sodium acetate and the like. Examples of suspending agents include stearyl triethanolamine, sodium lauryl sulfate, lauryl amino propionic acid, lecithin, benzalkonium chloride, benzethonium chloride, glycerin monostearate and other surfactants; polyvinyl alcohol, polyvinyl pyrrolidone, carboxymethyl cellulose sodium, methyl cellulose, hydroxymethyl cellulose, hydroxyethyl cellulose, hydroxypropyl cellulose and other hydrophilic polymers; and polysorbates, polyoxyethylene hardened castor oil and the like. Examples of buffers include buffers of phosphate salts, acetate salts, carbonate salts, citrate salts and the like. Examples of viscosity improvers include natural gums, cellulose derivatives and the like. Examples of emulsifiers include fatty acid esters (such as sucrose fatty acid esters, glycerin fatty acid esters, sorbitan fatty acid esters, propylene glycol fatty acid esters and the like), waxes (such as beeswax, hydrogenated rapeseed oil, hydrogenated safflower oil, hydrogenated palm oil, sitosterol, stigmasterol, campesterol, brassicasterol, cocoa butter powder, carnauba wax, rice bran wax, Japan wax, paraffin and the like), lecithin (such as egg yolk lecithin, soy lecithin, etc.) and the like.

Examples of colorants include water-soluble edible tar pigments (such as food color red #2 and #3, food color yellow #4 and #5, food color blue #1 and #2 and other food colors), water-insoluble lake pigments (such as aluminum salts of the aforementioned water-soluble edible tar pigments and the like), natural pigments (such as β-carotene, chlorophyll, red iron oxide and the like) and others. Examples of sweeteners include sucrose, lactose, sodium saccharin, dipotassium glycyrrhizate, aspartame, stevia and the like. Examples of antioxidants include sulfites, ascorbic acid and alkaline metals salts and alkaline earth metal salts thereof.

Tablets, granules, grains and the like may be coated by ordinary methods with a coating material as an enteric coating or to mask the flavor or improve photostability or appearance. Examples of coating materials include sugar coatings, water-soluble film coating materials, enteric coating materials and the like. Examples of sugar coatings include sucrose, which can be combined with one or two or more of talc, precipitated calcium carbonate, gelatin, gum arabic, pullulan, carnauba wax or the like. Examples of water-soluble film coating materials include hydroxypropyl cellulose (HPC), hydroxypropyl methyl cellulose (HPMC), ethyl cellulose, hydroxyethyl cellulose, methyl hydroxyethyl cellulose and other cellulose polymers; polyvinyl acetal diethylamino acetate, aminoalkyl methacrylate copolymer-E (Eudragit®), polyvinylpyrrolidone and other synthetic polymers; and pullulan and other polysaccharides and the like. Examples of enteric film coating materials include hydroxypropyl methylcellulose phthalate, hydroxypropyl methylcellulose acetate succinate, carboxymethyl ethyl cellulose, cellulose acetate phthalate and other cellulose polymers; methacrylic acid copolymer L (Eudragit L®), methacrylic acid copolymer LD (Eudragit L-30D55®), methacrylic acid copolymer S (Eudragit S®) and other acrylic acid polymers; and shellac and other natural materials and the like. These coating materials may be used alone, or two or more may be combined in suitable proportions as a coating material, or two or more may be coated sequentially.

The content of the lactam ring-opened streptothricin derivative or salt thereof of the invention in the antimicrobial agent of the invention is normally approximately 0.01 wt % to approximately 100 wt % or preferably approximately 1 wt % to approximately 99 wt %.

The administered dose of the lactam ring-opened streptothricin derivative or salt thereof of the invention may be any within the effective range for achieving antimicrobial effects, and differs depending on the target disease, subject, administration method, symptoms and the like, but is normally approximately 0.001 to approximately 1,000 mg per day per 1 kg of body weight. More specifically, in the case of oral administration to a patient infected with pathogenic bacteria such as those described above, approximately 0.01 to approximately 100 mg or preferably approximately 0.05 to approximately 50 mg or more preferably approximately 0.1 to approximately 10 mg of the lactam ring-opened streptothricin derivative of the invention is administered per day per 1 kg of body weight. In the case of parenteral administration, approximately 0.001 to approximately 50 mg or preferably approximately 0.005 to approximately 20 mg or more preferably approximately 0.01 to approximately 10 mg of the lactam ring-opened streptothricin derivative of the invention is administered per day per 1 kg of body weight.

The invention further includes the following sequences:

SEQ ID NO 1

```
ATG CCC CCC GAG ACC GCC GCG CCC CCC GAG ACC GCC
GCG CCC GCC CGG CCG CTC CGC CCC GTA CAG GCC CTC
CTC GTC GTC GAC GTC CAA ACC GCG TTC GTC TCC GGG
GCC GAG GCG GTC CCC GAG GCG GCC CGG GTC CTG GAC
CGC ACC CGT GGC CTG CTC GCC CGC GCC CGC ACC GCC
GGC GCC CTC GTC GTC CAC CTC CAG AAC GAC GGC GCG
CCC GGC GCC GTC GAC GCA CCG CAC ACC CCC GGC TGG
GAA CTC CAC CTC CCC GTC GAG CCC GGC CCC CGC GAG
CAC GTG GTC CGC AAG ACC GAG GAC GAC GGC TTC GCG
GAC ACC GGG CTC GGC GCC CTG CTC GAC GCT GCG GGC
GTG ACC GAA CTG GCG GTG TGC GGG GTG CTC TCC GAA
ATG TGC GTC GCC GCC ACC GCG CGC ACC GCC CTG GAG
CTG GGC CAC CGC GTC GTC CTC CCG CAC GAC GCG CAC
GCC ACC TAC GAC ATC CCC GCC GCG CCC GAC ATC AGC
GAC ACC GTC CCG GCC GCG ATG TCC TCC CGG GCC GCG
GAG TGG GCC CTC GGC GAC GAG GTC GAG ATC GTC CCG
CGC GCC GCC GCG GTC CCC TTC GTC GCC CCG CCG CTG
GCG CCC GCC CCC GAG GCC CCC GCT GCC GCC GCT GCA
CCC GCG GCC GGT ACG GGG CTC AGC CCT GCT GGT CCG
CCG CCC GCT CCA GCG CGC TGA
```

SEQ ID NO 2

```
Met Pro Pro Glu Thr Ala Ala Pro Pro Glu Thr Ala
Ala Pro Ala Arg Pro Leu Arg Pro Val Gln Ala Leu
```

-continued

```
Leu Val Val Asp Val Gln Thr Ala Phe Val Ser Gly
Ala Glu Ala Val Pro Glu Ala Ala Arg Val Leu Asp
Arg Thr Arg Gly Leu Leu Ala Arg Ala Arg Thr Ala
Gly Ala Leu Val Val His Leu Gln Asn Asp Gly Ala
Pro Gly Ala Val Asp Ala Pro His Thr Pro Gly Trp
Glu Leu His Leu Pro Val Glu Pro Gly Pro Arg Glu
His Val Val Arg Lys Thr Glu Asp Asp Gly Phe Ala
Asp Thr Gly Leu Gly Ala Leu Leu Asp Ala Ala Gly
Val Thr Glu Leu Ala Val Cys Gly Val Leu Ser Glu
Met Cys Val Ala Ala Thr Ala Arg Thr Ala Leu Glu
Leu Gly His Arg Val Val Leu Pro His Asp Ala His
Ala Thr Tyr Asp Ile Pro Ala Ala Pro Asp Ile Ser
Asp Thr Val Pro Ala Ala Met Ser Ser Arg Ala Ala
Glu Trp Ala Leu Gly Asp Glu Val Glu Ile Val Pro
Arg Ala Ala Ala Val Pro Phe Val Ala Pro Pro Leu
Ala Pro Ala Pro Glu Ala Pro Ala Ala Ala Ala Ala
Pro Ala Ala Gly Thr Gly Leu Ser Pro Ala Gly Pro
Pro Pro Ala Pro Ala Arg
```

SEQ ID NO 3

```
GTG ACC GCC ATG CCC CCC GAG ACC GCC GCG CCC CCC
GAG ACC GCC GCG CCC GCC CGG CCG CTC CGC CCC GTA
CAG GCC CTC CTC GTC GTC GAC GTC CAA ACC GCG TTC
GTC TCC GGG GCC GAG GCG GTC CCC GAG GCG GCC CGG
GTC CTG GAC CGC ACC CGT GGC CTG CTC GCC CGC GCC
CGC ACC GCC GGC GCC GTC GTC GTC CAC CTC CAG AAC
GAC GGC GCG CCC GGC GCC GTC GAC GCA CCG CAC ACC
CCC GGC TGG GAA CTC CAC CTC CCC GTC GAG CCC GGC
CCC CGC GAG CAC GTG GTC CGC AAG ACC GAG GAC GAC
GGC TTC GCG GAC ACC GGG CTC GGC GCC CTG CTC GAC
GCT GCG GGC GTG ACC GAA CTG GCG GTG TGC GGG GTG
CTC TCC GAA ATG TGC GTC GCC GCC ACC GCG CGC ACC
GCC CTG GAG CTG GGC CAC CGC GTC GTC CTC CCG CAC
GAC GCG CAC GCC ACC TAC GAC ATC CCC GCC GCG CCC
GAC ATC AGC GAC ACC GTC CCG GCC GCG ATG TCC TCC
CGG GCC GCG GAG TGG GCC CTC GGC GAC GAG GTC GAG
ATC GTC CCG CGC GCC GCC GCG GTC CCC TTC GTC GCC
CCG CCG CTG GCG CCC GCC CCC GAG GCC CCC GCT GCC
GCC GCT GCA CCC GCG GCC GGT ACG GGG CTC AGC CCT
GCT GGT CCG CCG CCC GCT CCA GCG CGC TGA
```

SEQ ID NO 4

```
Val Thr Ala Met Pro Pro Glu Thr Ala Ala Pro Pro
Glu Thr Ala Ala Pro Ala Arg Pro Leu Arg Pro Val
Gln Ala Leu Leu Val Val Asp Val Gln Thr Ala Phe
Val Ser Gly Ala Glu Ala Val Pro Glu Ala Ala Arg
Val Leu Asp Arg Thr Arg Gly Leu Leu Ala Arg Ala
Arg Thr Ala Gly Ala Leu Val Val His Leu Gln Asn
Asp Gly Ala Pro Gly Ala Val Asp Ala Pro His Thr
Pro Gly Trp Glu Leu His Leu Pro Val Glu Pro Gly
Pro Arg Glu His Val Val Arg Lys Thr Glu Asp Asp
Gly Phe Ala Asp Thr Gly Leu Gly Ala Leu Leu Asp
Ala Ala Gly Val Thr Glu Leu Ala Val Cys Gly Val
Leu Ser Glu Met Cys Val Ala Ala Thr Ala Arg Thr
Ala Leu Glu Leu Gly His Arg Val Val Leu Pro His
Asp Ala His Ala Thr Tyr Asp Ile Pro Ala Ala Pro
Asp Ile Ser Asp Thr Val Pro Ala Ala Met Ser Ser
Arg Ala Ala Glu Trp Ala Leu Gly Asp Glu Val Glu
Ile Val Pro Arg Ala Ala Ala Val Pro Phe Val Ala
Pro Pro Leu Ala Pro Ala Pro Glu Ala Pro Ala Ala
Ala Ala Ala Pro Ala Ala Gly Thr Gly Leu Ser Pro
Ala Gly Pro Pro Pro Ala Pro Ala Arg
```

SEQ ID NO 5

```
ATG CCC GCC GTG ACC GCC ATG CCC CCC GAG ACC GCC
GCG CCC CCC GAG ACC GCC GCG CCC GCC CGG CCG CTC
CGC CCC GTA CAG GCC CTC CTC GTC GTC GAC GTC CAA
ACC GCG TTC GTC TCC GGG GCC GAG GCG GTC CCC GAG
GCG GCC CGG GTC CTG GAC CGC ACC CGT GGC CTG CTC
GCC CGC GCC CGC ACC GCC GGC GCC CTC GTC GTC CAC
CTC CAG AAC GAC GGC GCG CCC GGC GCC GTC GAC GCA
CCG CAC ACC CCC GGC TGG GAA CTC CAC CTC CCC GTC
GAG CCC GGC CCC CGC GAG CAC GTG GTC CGC AAG ACC
GAG GAC GAC GGC TTC GCG GAC ACC GGG CTC GGC GCC
CTG CTC GAC GCT GCG GGC GTG ACC GAA CTG GCG GTG
TGC GGG GTG CTC TCC GAA ATG TGC GTC GCC GCC ACC
GCG CGC ACC GCC CTG GAG CTG GGC CAC CGC GTC GTC
CTC CCG CAC GAC GCG CAC GCC ACC TAC GAC ATC CCC
GCC GCG CCC GAC ATC AGC GAC ACC GTC CCG GCC GCG
ATG TCC TCC CGG GCC GCG GAG TGG GCC CTC GGC GAC
```

-continued

GAG GTC GAG ATC GTC CCG CGC GCC GCC GCG GTC CCC
TTC GTC GCC CCG CCG CTG GCG CCC GCC CCC GAG GCC
CCC GCT GCC GCC GCT GCA CCC GCG GCC GGT ACG GGG
CTC AGC CCT GCT GGT CCG CCG CCC GCT CCA GCG CGC
TGA

SEQ ID NO 6

Met Pro Ala Val Thr Ala Met Pro Pro Glu Thr Ala
Ala Pro Pro Glu Thr Ala Ala Pro Ala Arg Pro Leu
Arg Pro Val Gln Ala Leu Leu Val Val Asp Val Gln
Thr Ala Phe Val Ser Gly Ala Glu Ala Val Pro Glu
Ala Ala Arg Val Leu Asp Arg Thr Arg Gly Leu Leu
Ala Arg Ala Arg Thr Ala Gly Ala Leu Val Val His
Leu Gln Asn Asp Gly Ala Pro Gly Ala Val Asp Ala
Pro His Thr Pro Gly Trp Glu Leu His Leu Pro Val
Glu Pro Gly Pro Arg Glu His Val Val Arg Lys Thr
Glu Asp Asp Gly Phe Ala Asp Thr Gly Leu Gly Ala
Leu Leu Asp Ala Ala Gly Val Thr Glu Leu Ala Val
Cys Gly Val Leu Ser Glu Met Cys Val Ala Ala Thr
Ala Arg Thr Ala Leu Glu Leu Gly His Arg Val Val
Leu Pro His Asp Ala His Ala Thr Tyr Asp Ile Pro
Ala Ala Pro Asp Ile Ser Asp Thr Val Pro Ala Ala
Met Ser Ser Arg Ala Ala Glu Trp Ala Leu Gly Asp
Glu Val Glu Ile Val Pro Arg Ala Ala Ala Val Pro
Phe Val Ala Pro Pro Leu Ala Pro Ala Pro Glu Ala
Pro Ala Ala Ala Ala Ala Pro Ala Ala Gly Thr Gly
Leu Ser Pro Ala Gly Pro Pro Pro Ala Pro Ala Arg

SEQ ID NO 7

ATG ACC GCC ATG CCC GCC GTG ACC GCC ATG CCC CCC
GAG ACC GCC GCG CCC CCC GAG ACG GCC GCG CCC GCC
CGG CCG CTC CGC CCC GTA CAG GCC CTC CTC GTC GTC
GAC GTC CAA ACC GCG TTC GTC TCC GGG GCC GAG GCG
GTC CCC GAG GCG GCC CGG GTC CTG GAC CGC ACC CGT
GGC CTG CTC GCC CGC GCC CGC ACC GCC GGC GCC CTC
GTC GTC CAC CTC CAG AAC GAC GGC GCG CCC GGC GCC
GTC GAC GCA CCG CAC ACC CCC GGC TGG GAA CTC CAC
CTC CCC GTC GAG CCC GGC CCC CGC GAG CAC GTG GTC
CGC AAG ACC GAG GAC GAC GGC TTC GCG GAC ACC GGG
CTC GGC GCC CTG CTC GAC GCT GCG GGC GTG ACC GAA
CTG GCG GTG TGC GGG GTG CTC TCC GAA ATG TGC GTC
GCC GCC ACC GCG CGC ACC GCC CTG GAG CTG GGC CAC
CGC GTC GTC CTC CCG CAC GAC GCG CAC GCC ACC TAC
GAC ATC CCC GCC GCG CCC GAC ATC AGC GAC ACC GTC
CCG GCC GCG ATG TCC TCC CGG GCC GCG GAG TGG GCC
CTC GGC GAC GAG GTC GAG ATC GTC CCG CGC GCC GCC
GCG GTC CCC TTC GTC GCC CCG CCG CTG GCG CCC GCC
CCC GAG GCC CCC GCT GCC GCC GCT GCA CCC GCG GCC
GGT ACG GGG CTC AGC CCT GCT GGT CCG CCG CCC GCT
CCA GCG CGC TGA

SEQ ID NO 8

Met Thr Ala Met Pro Ala Val Thr Ala Met Pro Pro
Glu Thr Ala Ala Pro Pro Glu Thr Ala Ala Pro Ala
Arg Pro Leu Arg Pro Val Gln Ala Leu Leu Val Val
Asp Val Gln Thr Ala Phe Val Ser Gly Ala Glu Ala
Val Pro Glu Ala Ala Arg Val Leu Asp Arg Thr Arg
Gly Leu Leu Ala Arg Ala Arg Thr Ala Gly Ala Leu
Val Val His Leu Gln Asn Asp Gly Ala Pro Gly Ala
Val Asp Ala Pro His Thr Pro Gly Trp Glu Leu His
Leu Pro Val Glu Pro Gly Pro Arg Glu His Val Val
Arg Lys Thr Glu Asp Asp Gly Phe Ala Asp Thr Gly
Leu Gly Ala Leu Leu Asp Ala Ala Gly Val Thr Glu
Leu Ala Val Cys Gly Val Leu Ser Glu Met Cys Val
Ala Ala Thr Ala Arg Thr Ala Leu Glu Leu Gly His
Arg Val Val Leu Pro His Asp Ala His Ala Thr Tyr
Asp Ile Pro Ala Ala Pro Asp Ile Ser Asp Thr Val
Pro Ala Ala Met Ser Ser Arg Ala Ala Glu Trp Ala
Leu Gly Asp Glu Val Glu Ile Val Pro Arg Ala Ala
Ala Val Pro Phe Val Ala Pro Pro Leu Ala Pro Ala
Pro Glu Ala Pro Ala Ala Ala Ala Ala Pro Ala Ala
Gly Thr Gly Leu Ser Pro Ala Gly Pro Pro Pro Ala
Pro Ala Arg

SEQ ID NO 9

ATG ACC CCC ATG ACC GCC ATG CCC GCC GTG ACC GCC
ATG CCC CCC GAG ACC GCC GCG CCC CCC GAG ACC GCC
GCG CCC GCC CGG CCG CTC CGC CCC GTA CAG GCC CTC
CTC GTC GTC GAC GTC CAA ACC GCG TTC GTC TCC GGG
GCC GAG GCG GTC CCC GAG GCG GCC CGG GTC CTG GAC

-continued

CGC ACC CGT GGC CTG CTC GCC CGC GCC CGC ACC GCC
GGC GCC CTC GTC GTC CAC CTC CAG AAC GAC GGC GCG
CCC GGC GCC GTC GAC GCA CCG CAC ACC CCC GGC TGG
GAA CTC CAC CTC CCC GTC GAG CCC GGC CCC CGC GAG
CAC GTG GTC CGC AAG ACC GAG GAC GAC GGC TTC GCG
GAC ACC GGG CTC GGC GCC CTG CTC GAC GCT GCG GGC
GTG ACC GAA CTG GCG GTG TGC GGG GTG CTC TCC GAA
ATG TGC GTC GCC GCC ACC GCG CGC ACC GCC CTG GAG
CTG GGC CAC CGC GTC GTC CTC CCG CAC GAC GCG CAC
GCC ACC TAC GAC ATC CCC GCC GCG CCC GAC ATC AGC
GAC ACC GTC CCG GCC GCG ATG TCC TCC CGG GCC GCG
GAG TGG GCC CTC GGC GAC GAG GTC GAG ATC GTC CCG
CGC GCC GCC GCG GTC CCC TTC GTC GCG CCG CCG CTG
GCG CCC GCC CCC GAG GCC CCC GCT GCC GCC GCT GCA
CCC GCG GCC GGT ACG GGG CTC AGC CCT GCT GGT CCG
CCG CCC GCT CCA GCG CGC TGA

SEQ ID NO 10

Met Thr Pro Met Thr Ala Met Pro Ala Val Thr Ala
Met Pro Pro Glu Thr Ala Ala Pro Pro Glu Thr Ala
Ala Pro Ala Arg Pro Leu Arg Pro Val Gln Ala Leu
Leu Val Val Asp Val Gln Thr Ala Phe Val Ser Gly
Ala Glu Ala Val Pro Glu Ala Ala Arg Val Leu Asp
Arg Thr Arg Gly Leu Leu Ala Arg Ala Arg Thr Ala
Gly Ala Leu Val Val His Leu Gln Asn Asp Gly Ala
Pro Gly Ala Val Asp Ala Pro His Thr Pro Gly Trp
Glu Leu His Leu Pro Val Glu Pro Gly Pro Arg Glu
His Val Val Arg Lys Thr Glu Asp Asp Gly Phe Ala
Asp Thr Gly Leu Gly Ala Leu Leu Asp Ala Ala Gly
Val Thr Glu Leu Ala Val Cys Gly Val Leu Ser Glu
Met Cys Val Ala Ala Thr Ala Arg Thr Ala Leu Glu
Leu Gly His Arg Val Val Leu Pro His Asp Ala His
Ala Thr Tyr Asp Ile Pro Ala Ala Pro Asp Ile Ser
Asp Thr Val Pro Ala Ala Met Ser Ser Arg Ala Ala
Glu Trp Ala Leu Gly Asp Glu Val Glu Ile Val Pro
Arg Ala Ala Ala Val Pro Phe Val Ala Pro Pro Leu
Ala Pro Ala Pro Glu Ala Pro Ala Ala Ala Ala Ala
Pro Ala Ala Gly Thr Gly Leu Ser Pro Ala Gly Pro
Pro Pro Ala Pro Ala Arg

SEQ ID NO 11

ATG ATG ACC CCC ATG ACC GCC ATG CCC GCC GTG ACC
GCC ATG CCC CCC GAG ACC GCC GCG CCC CCC GAG ACC
GCC GCG CCC GCC CGG CCG CTC CGC CCC GTA CAG GCC
CTC CTC GTC GTC GAC GTC CAA ACC GCG TTC GTC TCC
GGG GCC GAG GCG GTC CCC GAG GCG GCC CGG GTC CTG
GAC CGC ACC CGT GGC CTG CTC GCC CGC GCC CGC ACC
GCC GGC GCC CTC GTC GTC CAC CTC CAG AAC GAC GGC
GCG CCC GGC GCC GTC GAC GCA CCG CAC ACC CCC GGC
TGG GAA CTC CAC CTC CCC GTC GAG CCC GGC CCC CGC
GAG CAC GTG GTC CGC AAG ACC GAG GAC GAC GGC TTC
GCG GAC ACC GGG CTC GGC GCC CTG CTC GAC GCT GCG
GGC GTG ACC GAA CTG GCG GTG TGC GGG GTG CTC TCC
GAA ATG TGC GTC GCC GCC ACC GCG CGC ACC GCC CTG
GAG CTG GGC CAC CGC GTC GTC CTC CCG CAC GAC GCG
CAC GCC ACC TAC GAC ATC CCC GCC GCG CCC GAC ATC
AGC GAC ACC GTC CCG GCC GCG ATG TCC TCC CGG GCC
GCG GAG TGG GCC CTC GGC GAC GAG GTC GAG ATC GTC
CCG CGC GCC GCC GCG GTC CCC TTC GTC GCC CCG CCG
CTG GCG CCC GCC CCC GAG GCC CCC GCT GCC GCC GCT
GCA CCC GCG GCC GGT ACG GGG CTC AGC CCT GCT GGT
CCG CCG CCC GCT CCA GCG CGC TGA

SEQ ID NO 12

Met Met Thr Pro Met Thr Ala Met Pro Ala Val Thr
Ala Met Pro Pro Glu Thr Ala Ala Pro Pro Glu Thr
Ala Ala Pro Ala Arg Pro Leu Arg Pro Val Gln Ala
Leu Leu Val Val Asp Val Gln Thr Ala Phe Val Ser
Gly Ala Glu Ala Val Pro Glu Ala Ala Arg Val Leu
Asp Arg Thr Arg Gly Leu Leu Ala Arg Ala Arg Thr
Ala Gly Ala Leu Val Val His Leu Gln Asn Asp Gly
Ala Pro Gly Ala Val Asp Ala Pro His Thr Pro Gly
Trp Glu Leu His Leu Pro Val Glu Pro Gly Pro Arg
Glu His Val Val Arg Lys Thr Glu Asp Asp Gly Phe
Ala Asp Thr Gly Leu Gly Ala Leu Leu Asp Ala Ala
Gly Val Thr Glu Leu Ala Val Cys Gly Val Leu Ser
Glu Met Cys Val Ala Ala Thr Ala Arg Thr Ala Leu
Glu Leu Gly His Arg Val Val Leu Pro His Asp Ala

-continued

His Ala Thr Tyr Asp Ile Pro Ala Ala Pro Asp Ile
Ser Asp Thr Val Pro Ala Ala Met Ser Ser Arg Ala
Ala Glu Trp Ala Leu Gly Asp Glu Val Glu Ile Val
Pro Arg Ala Ala Ala Val Pro Phe Val Ala Pro Pro
Leu Ala Pro Ala Pro Glu Ala Pro Ala Ala Ala Ala
Ala Pro Ala Ala Gly Thr Gly Leu Ser Pro Ala Gly
Pro Pro Pro Ala Pro Ala Arg

SEQ ID NO 13

GTG CCG CGT TCG ACG ATG ATG ACC CCC ATG ACC GCC
ATG CCC GCC GTG ACC GCC ATG CCC CCC GAG ACC GCC
GCG CCC CCC GAG ACC GCC GCG CCC GCC CGG CCG CTC
CGC CCC GTA CAG GCC CTC CTC GTC GTC GAC GTC CAA
ACC GCG TTC GTC TCC GGG GCC GAG GCG GTC CCC GAG
GCG GCC CGG GTC CTG GAC CGC ACC CGT GGC CTG CTC
GCC CGC GCC CGC ACC GCC GGC GCC CTC GTC GTC CAC
CTC CAG AAC GAC GGC GCG CCC GGC GCC GTC GAC GCA
CCG CAC ACC CCC GGC TGG GAA CTC CAC CTC CCC GTC
GAG CCC GGC CCC CGC GAG CAC GTG GTC CGC AAG ACC
GAG GAC GAC GGC TTC GCG GAC ACC GGG CTC GGC GCC
CTG CTC GAC GCT GCG GGC GTG ACC GAA CTG GCG GTG
TGC GGG GTG CTC TCC GAA ATG TGC GTC GCC GCC ACC
GCG CGC ACC GCC CTG GAG CTG GGC CAC CGC GTC GTC
CTC CCG CAC GAC GCG CAC GCC ACC TAC GAC ATC CCC
GCC GCG CCC GAC ATC AGC GAC ACC GTC CCG GCC GCG
ATG TCC TCC CGG GCC GCG GAG TGG GCC CTC GGC GAC
GAG GTC GAG ATC GTC CCG CGC GCC GCC GCG GTC CCC
TTC GTC GCC CCG CCG CTG GCG CCC GCC CCC GAG GCC
CCC GCT GCC GCC GCT GCA CCC GCG GCC GGT ACG GGG
CTC AGC CCT GCT GGT CCG CCG CCC GCT CCA GCG CGC
TGA

SEQ ID NO 14

Val Pro Arg Ser Thr Met Met Thr Pro Met Thr Ala
Met Pro Ala Val Thr Ala Met Pro Pro Glu Thr Ala
Ala Pro Pro Glu Thr Ala Ala Pro Ala Arg Pro Leu
Arg Pro Val Gln Ala Leu Leu Val Val Asp Val Gln
Thr Ala Phe Val Ser Gly Ala Glu Ala Val Pro Glu
Ala Ala Arg Val Leu Asp Arg Thr Arg Gly Leu Leu
Ala Arg Ala Arg Thr Ala Gly Ala Leu Val Val His
Leu Gln Asn Asp Gly Ala Pro Gly Ala Val Asp Ala
Pro His Thr Pro Gly Trp Glu Leu His Leu Pro Val
Glu Pro Gly Pro Arg Glu His Val Val Arg Lys Thr
Glu Asp Asp Gly Phe Ala Asp Thr Gly Leu Gly Ala
Leu Leu Asp Ala Ala Gly Val Thr Glu Leu Ala Val
Cys Gly Val Leu Ser Glu Met Cys Val Ala Ala Thr
Ala Arg Thr Ala Leu Glu Leu Gly His Arg Val Val
Leu Pro His Asp Ala His Ala Thr Tyr Asp Ile Pro
Ala Ala Pro Asp Ile Ser Asp Thr Val Pro Ala Ala
Met Ser Ser Arg Ala Ala Glu Trp Ala Leu Gly Asp
Glu Val Glu Ile Val Pro Arg Ala Ala Ala Val Pro
Phe Val Ala Pro Pro Leu Ala Pro Ala Pro Glu Ala
Pro Ala Ala Ala Ala Ala Pro Ala Ala Gly Thr Gly
Leu Ser Pro Ala Gly Pro Pro Pro Ala Pro Ala Arg

SEQ ID NO 15

ATG ATC CGC CCG GAT CGA TGC CCG TGG CAA CCA TGC
CCG TCC GGC CGG TAC CTT TCC CGC CCG TCC GGC CGA
GTG CCG CGT TCG ACG ATG ATG ACC CCC ATG ACC GCC
ATG CCC GCC GTG ACC GCC ATG CCC CCC GAG ACC GCC
GCG CCC CCC GAG ACC GCC GCG CCC GCC CGG CCG CTC
CGC CCC GTA CAG GCC CTC CTC GTC GTC GAC GTC CAA
ACC GCG TTC GTC TCC GGG GCC GAG GCG GTC CCC GAG
GCG GCC CGG GTC CTG GAC CGC ACC CGT GGC CTG CTC
GCC CGC GCC CGC ACC GCC GGC GCC CTC GTC GTC CAC
CTC CAG AAC GAC GGC GCG CCC GGC GCC GTC GAC GCA
CCG CAC ACC CCC GGC TGG GAA CTC CAC CTC CCC GTC
GAG CCC GGC CCC CGC GAG CAC GTG GTC CGC AAG ACC
GAG GAC GAC GGC TTC GCG GAC ACC GGG CTC GGC GCC
CTG CTC GAC GCT GCG GGC GTG ACC GAA CTG GCG GTG
TGC GGG GTG CTC TCC GAA ATG TGC GTC GCC GCC ACC
GCG CGC ACC GCC CTG GAG CTG GGC CAC CGC GTC GTC
CTC CCG CAC GAC GCG CAC GCC ACC TAC GAC ATC CCC
GCC GCG CCC GAC ATC AGC GAC ACC GTC CCG GCC GCG
ATG TCC TCC CGG GCC GCG GAG TGG GCC CTC GGC GAC
GAG GTC GAG ATC GTC CCG CGC GCC GCC GCG GTC CCC
TTC GTC GCC CCG CCG CTG GCG CCC GCC CCC GAG GCC
CCC GCT GCC GCC GCT GCA CCC GCG GCC GGT ACG GGG
CTC AGC CCT GCT GGT CCG CCG CCC GCT CCA GCG CGC
TGA

-continued

SEQ ID NO 16

Met Ile Arg Pro Asp Arg Cys Pro Trp Gln Pro Cys
Pro Ser Gly Arg Tyr Leu Ser Arg Pro Ser Gly Arg
Val Pro Arg Ser Thr Met Met Thr Pro Met Thr Ala
Met Pro Ala Val Thr Ala Met Pro Pro Glu Thr Ala
Ala Pro Pro Glu Thr Ala Ala Pro Ala Arg Pro Leu
Arg Pro Val Gln Ala Leu Leu Val Val Asp Val Gln
Thr Ala Phe Val Ser Gly Ala Glu Ala Val Pro Glu
Ala Ala Arg Val Leu Asp Arg Thr Arg Gly Leu Leu
Ala Arg Ala Arg Thr Ala Gly Ala Leu Val Val His
Leu Gln Asn Asp Gly Ala Pro Gly Ala Val Asp Ala
Pro His Thr Pro Gly Trp Glu Leu His Leu Pro Val
Glu Pro Gly Pro Arg Glu His Val Val Arg Lys Thr
Glu Asp Asp Gly Phe Ala Asp Thr Gly Leu Gly Ala
Leu Leu Asp Ala Ala Gly Val Thr Glu Leu Ala Val
Cys Gly Val Leu Ser Glu Met Cys Val Ala Ala Thr
Ala Arg Thr Ala Leu Glu Leu Gly His Arg Val Val
Leu Pro His Asp Ala His Ala Thr Tyr Asp Ile Pro
Ala Ala Pro Asp Ile Ser Asp Thr Val Pro Ala Ala
Met Ser Ser Arg Ala Ala Glu Trp Ala Leu Gly Asp
Glu Val Glu Ile Val Pro Arg Ala Ala Ala Val Pro
Phe Val Ala Pro Pro Leu Ala Pro Ala Pro Glu Ala
Pro Ala Ala Ala Ala Ala Pro Ala Ala Gly Thr Gly
Leu Ser Pro Ala Gly Pro Pro Pro Ala Pro Ala Arg

SEQ ID NO 17

GACGCNGANGCNATCGANGNNCTNGA

SEQ ID NO 18

GTTSTNGTTNGTNACNTCNAGCCA

SEQ ID NO 19

GGGGGATCCACCACTCTTGACGACACGGCT

SEQ ID NO 20

ACCAAGCTTTCAGGGGCAGGGCATGCTCAT

SEQ ID NO 21

ACCAAGCTTAATATGACCACTCTTGACGACACG

SEQ ID NO 22

AAACTGCAGTCAGGGGCAGGGCATGCTCAT

SEQ ID NO 23

ACCAAGCTTACCATGCCCCCCGAGACCGCC GCG

SEQ ID NO 24

AAACTGCAGTCAGCGCGCTGGAGCGGGCGG

SEQ ID NO 25

CTCGAACCCCGGTGCGCAGCGGCCGTTGACGGTGACAGCCTCCACGG
TGGCCCTCCTCGCGTCGTCGCGGTGOGGTCGGATGCCGCGCCCCGCC
GCACGGAACGCCCACGCACGGAACCGACGCGCGCACGGCCGGAGCAC
CTACGGATGATCCGCCCGGATCGATGCCCGTGGCAACCATGCCCGTC
CGGCCGGTACCTTTCCCGCCCGTCCGGCCGAGTGCCGCGTTCGACGA
TGATGACCCCCATGACCGCCATGCCCGCCGTGACCGCCATGCCCCCC
GAGACCGCCGCGCCCCCCGAGACCGCCGCGCCCGCCCGGCCGCTCCG
CCCCCGTACAGGCCCTCCTCGTCGTCGACGTCCAAACGCGTTCGTCT
CCGGGGCCGAGGCGGTCCCCGAGGCGGCCCGGGTCCTGGACCGCACC
CGTGGCCTGCTCGCCCGCGCCCGCACCGCCGGCGCCCTCGTCGTCCA
CCTCCAGAACGACGGCGCGCCCGGCGCCGTCGACGCACCGCACACCC
CCGGCTGGGAACTCCACCTCCCCGTCGAGCCCGGCCCCCGCGAGCAC
GTGGTCCGCAAGACCGAGGACGACGGCTTCGCGGACACCGGGCTCGG
CGCCCTGCTCGACGCTGCGGGCGTGACCGAACTGGCGGTGTGCGGGG
TGCTCTCCGAAATGTGCGTCGCCGCCACCGCGCGCACCGCCCTGGAG
CTGGGCCACCGCGTCGTCCTCCCGCACGACGCGCACGCCACCTACGA
CATCCCCGCCGCGCCCGACATCAGCGACACCGTCCCGGCCGCGATGT
CCTCCCGGGCCGCGGAGTGGGCCCTCGGCGACGGAGGTCGAGATCTC
CCGCGCGCCGCCGCGGTCCCCTTCGTCGCCCCGCCGCTGGCGCCCGC
CCCCGAGGCCCCCGCTGCCGCCGCTGCACCCGCGGCCGGTACGGGGC
TCAGCCCTGCTGGTCCGCCGCCCGCTCCAGCGCGCTGA

SEQ ID NO 26

MIRPDRCPWQPCPSGRYLSRPSGRVPRSTMMTPMTAMPAVTAMPPET
AAPPETAAPARPLRPVQALLWDVOTAFVSGAEAVPEAARVLDRTRGL
LARARTAGALVVHLQNDGAPGAVDAPHTPGWELHILPVEPGPREHVV
RKTEDDGFADTGLGALDAAGVTELAVCGVLSEMCVAATARTALELGH
RWLPHDAHATYDIPAAPDISDTVPAAMSSRAAEWALGDEVEIVPRAA
AVPFVAPPLAPAPEAPAAAAAPAAGTGLSPAGPPPAPAR

EXAMPLES

The invention is explained in more detail below based on examples, but the invention is not limited to these examples.

Materials and Methods

First, the materials and experimental methods used in the invention are explained.

(1) Chemicals

Streptothricins (ST) (ClonNAT, a mixture of ST-F and ST-D in proportions of roughly 5:1) were obtained from Werner BioAgents (Meisenweg, Jena, Germany). All other chemicals were all analytical grade.

(2) Bacterial Strains, Plasmids and General Techniques for DNA Manipulation

*S. albulus* NBRC14147 DNA was used for cloning the sttH gene. The media and growth conditions for *S. albulus* NBRC14147 have been previously described (Takagi, H., Hoshino, Y., Nakamori, S. & Inoue, S., *J. Biosci. Bioeng.*, 39, 94-96 (2000)). The *E. coli-Streptomyces* shuttle vector pWHM3 (Kieser, T., Bibb, M. J., Buttner, M. J., Chater, K. F. & Hopwood, D. A., PRACTICAL STREPTOMYCES GENETICS (John Innes Foundation, Norwich, U.K., (2000)) and *S. Lividans* TK23 (Kieser, T., Bibb, M. J., Buttner, M. J., Chater, K. F. & Hopwood, D. A., PRACTICAL STREPTOMYCES GENETICS (John Innes Foundation, Norwich, U.K.) (2000)) were employed for cloning the sttH gene. *S. lavendulae* NBRC12789 was used as an ST-producing strain. The nat gene encoding NAT for STs was excised from the pHN15 plasmid (Werner Bio-Agents). The pQE30 plasmid, *E. coli* M15 (pREP4) (Qiagen) and *E. coli* XL1-Blue MRF' (Toyobo, Osaka, Japan) were used for overexpression of the recombinant protein. DNA recombination of the *E. coli* and *Streptomyces* strains was accomplished by standard techniques (Kieser, T., Bibb, M. J., Buttner, M. J., Chater, K. F. & Hopwood, D. A., PRACTICAL STREPTOMYCES GENETICS (John Innes Foundation, Norwich, U.K.) (2000); Sambrook, J. & Russell, D. W., MOLECULAR CLONING: A LABORATORY MANUAL (Cold Spring Harbor Lab. Press, Plainview, N.Y.) (2001)). Southern blotting was performed using an ECL Direct Nucleic Acid Labeling and Detection System (Amersham Bioscience, Piscataway, N.J.). The *S. cerevisiae* CKY8 strain (MATα ura3-52 leu2-3, 112) and the yeast episomal plasmid pAD4 were employed for expressing the sttH and nat genes in *S. cerevisiae*. This plasmid is an *E. coli-Saccharomyces* shuttle vector comprising an ampicillin resistance gene (for *E. coli*) and LEU2 gene (for yeast) as selection markers. The CKY8 strain was transformed using a BD Yeastmaker Yeast Transformation System 2 (BD Biosciences Clontech, Palo Alto, Calif.). *S. cerevisiae* CKY8 strains carrying pAD4 derivatives were grown in synthetic complete medium lacking L-leucine (SC-Leu) (Sherman, F., *Methods Enzymol.* 194, 3-21 (1991)) or in YPD medium (Sherman, F., *Methods Enzymol.*, 194, 3-21 (1991)). The microorganisms *S. cerevisiae* S288C (same genetic background as CKY8), *S. pombe* L972, *E. coli* W3110, *B. subtilis* NBRC13169, *S. aureus* AB and *S. aureus* FIR1169 (Igarashi, H., Fujikawa, H., Usami, H., Kawabata, S. & Morita, T., *Infect. Immun.*, 44, 175-181 (1984)) were used in the minimum inhibitory concentration (MIC) tests for STs and ST-acids.

(3) PCR Amplification of Genes Coding for N-Acetyltransferase (NAT) in *Streptomyces* Strains Two primers, 5'GACGC(G/C)GA(A/G)GC(G/C)ATCGA (A/G)G(G/C)(G/C)CT (G/C)GA-3' (SEQ ID NO: 17) and 5'-GTTST(C/T)GTT(G/C)GT(G/C)AC (C/T)TC (G/C) AGCCA-3' (SEQ ID NO: 18), were designed based on the highly conserved amino acid sequence of the NATs from *S. lavendulae* (Horinouchi, S. et al., *J. Bacteriol.*, 169, 1929-1937 (1987)), *S. rochei* (Fernandez-Moreno, M. A., Vallin, C. & Malpartida, F., *J. Bacteriol.*, 179, 6929-6936 (1997)) and *S. noursei* (Krugel, H., et al., *Gene*, 62, 209-217 (1988); Grammel, N. et al., *Eur. J. Biochem.* 269, 347-357 (2002)). PCR amplification was performed under the following conditions: denaturation at 94° C. for 1 minute, annealing at 60° C. for 1 minute, elongation at 72° C. for 1 minute, 30 cycles.

(4) Cloning of sttH Gene from *S. albulus* NBRC14147

*S. albulus* NBRC14147 genomic DNA was partially digested with Sau3AI. SAu3AI fragments exceeding 2.0 kb were ligated into the BamHI site of a pWHM3 plasmid carrying a thiostrepton resistance gene. *S. lividans* TK23 was transformed with the resulting recombinant DNA, and transformants exhibiting resistance to both STs (100 μg/mL) and thiostrepton (20 μg/mL) on R5 agar medium (Kieser, T. et al., PRACTICAL STREPTOMYCES GENETICS (John Innes Foundation, Norwich, U.K. (2000)) were isolated. Out of 13 transformants, 1 transformant carrying a plasmid with a 2.9 kb insert (pWHM3-st11) was selected for subsequent testing. The complete nucleotide sequence of this 2.9 kb fragment was determined, and two plasmids having ORF2-ORF3 (pWHM3-orf2-3) and ORF1 (pWHM3-orf1), respectively, were constructed using pWHM3.

(5) Estimation of sttH (ORF2) Gene Start Codon

For purposes of estimating the sttH gene start codon, 7 forward primers and 1 reverse primer were designed as shown schematically in FIG. 2, and used to amplify the sttH gene. Additional BamHI sites (5'-GGGGGATCC-3') were attached to all the forward primers, and an additional HindIII site (5'-ACCAAGCTT-3') to the reverse primer. PCR was performed under standard conditions. After sequence confirmation, each of the 7 amplified fragments was inserted into the same site of a pQE30 plasmid to prepare the plasmids pQE30-SHF1R (carrying PCR fragment amplified by SH-F1 and SH-R primers), pQE30-SHF2R (SH-F2 and SH-R), pQE30-SHF3R (SH-F3 and SH-R), pQE30-SHF4R (SH-F4 and SH-R), pQE30-SHF5R (SH-F5 and SH-R), pQE30-SHF6R (SH-F6 and SH-R) and pQE30-SBF7R (SH-F7 and SH-R). Each of the resulting plasmids was introduced into *E. coli* XL1-Blue MRF'. In these transformants, MICs of STs were determined on Luria-Bertani (LB) agar plates (Sambrook, J. & Russell, D. W., MOLECULAR CLONING: A LABORATORY MANUAL, Cold Spring Harbor Lab. Press, Plainview, N.Y. (2001)) containing ampicillin (100 μg/mL), 0.1 mM isopropyl-β-D-thiogalactoside (IPTG) and STs (0 to 100 μg/mL).

(6) Identification of ST-F and ST-D Derived Compounds Produced by SttH Recombinant Enzyme (rSttH), and rSttH Reaction Rate Test (Kinetic Analysis)

In accordance with the manufacturer's (Qiagen) protocols, a reaction mixture (500 μL) was prepared using 100 mM sodium phosphate buffer (pH 6.5), 1 mg/mL ST-F or ST-D, and 100 μg/mL of purified rSttH from *E. coli* M15 (pREP4) carrying pQE30-SHF6R. The reaction mixture was reacted for 1 hour at 30° C. with or without rSttH, and then extracted with chloroform to remove the proteins. The water layer was analyzed by reverse-phase HPLC using an ion-pair reagent. The analytical conditions were: column, $C_{18}$ reverse-phase column (COSMOSIL 5C18-AR—II, 250×4.6 mm, Nacalai Tesque, Kyoto, Japan); column temperature, 30° C.; detection, 210 nm; and flow rate, 1 mL/minute. Two different mobile phases were used, one of 0.1% heptafluorobutyric acid+18% acetonitrile (ST-F reaction) and one of 0.1% heptafluorobutyric acid+23% acetonitrile (ST-D reaction). The kinetic assays were performed under conditions similar to those described previously except that the enzyme concentrations (2 μg/mL) and reaction times (5 minutes) were reduced to make them compatible with measurement of steady-state kinetic parameters. All tests were carried out under linear conditions. The reactions were terminated by addition of 15 μl 2N HCl, and then analyzed by HPLC. The kinetic constants were estimated using a Lineweaver-Burk plot. The native molecular weight of the rSttH was estimated by gel filtration using a COSMOSIL 5Diol-300 (7.8 mm×600 mm) column (Nacalai Tesque) which had been equilibrated with 20 mM sodium phosphate buffer (pH 7.0) containing 100 mM sodium sulfate.

(7) Purification of ST Compounds (ST and ST-Derived Compounds)

ST-F and ST-D were purified from commercial STs by reverse-phase HPLC under basically the same conditions as described above apart from the column size (250×10 mm), flow rate (4.72 mL/minute) and acetonitrile concentration (25%). The organic solvent was removed from the HPLC fractions, and the aqueous layer was freeze dried to obtain white powders of the compounds. Enzymatically synthesized ST-F-acid and ST-D-acid were also purified by procedures similar to those described for ST-F and ST-D purification.

(8) Structural Determination of ST-F-Acid and ST-D-Acid

The ESI-MS/MS spectra of the ST compounds were calculated using a Finnigan MAT TSQ 7000 (quadrupole tandem mass spectrometer). The $^{1}$H-NMR spectrum data for ST-F-acid and ST-D-acid were recorded at 500 MHz using a JEOL LNM-LA500 spectrometer. (i) ST-F-acid, $^{1}$H-NMR (500 MHz, $D_2O$) δ: 1.60 (4H, m, H-17, 18), 2.51 (1H, dd, J=8 and 17 Hz, H-15), 2.62 (1H, dd, J=5 and 17 Hz, H-15),2.86 (2H, br s, H-19), 2.94 (1H, dd, J=10 and 13 Hz, H-4), 3.08 (1H, dd, J=3 and 13 Hz, H-3), 3.49 (1H, m, H-16), 3.55 (2H, d, J=6 Hz, H-12), 3.98 (2H, m, H-5), 3.99 (1H, t, J=3 Hz, H-9), 4.05 (1H, dd, J=3 and 10 Hz, H-8), 4.14 (1H, t, J=6 Hz, H-11), 4.31 (1H, d, J=5 Hz, H-2), 4.59 (1H, d, J=4 Hz, H-10), 4.95 (1H, d, J=9 Hz, H-7). (ii) ST-D-acid, $^{1}$H-NMR (500 MHz, $D_2O$) δ: 1.43 (4H, m, H-18, 24), 1.51 (4H, m, H-17, 23), 1.60 (4H, m, H-29, 30), 2.40 (1H, dd, J=8 and 16 Hz, H-27), 2.43 (1H, dd, J=8 and 16 Hz, H-21), 2.48 (1H, dd, J=8 and 16 Hz, H-15), 2.50 (1H, dd, J=5 and 17 Hz, H-27), 2.53 (1H, dd, J=5 and 17 Hz, H-21), 2.57 (1H, dd, J=5 and 17 Hz, H-15), 2.85 (2H, m, H-31), 2.86 (2H, br s, H-19), 2.94 (1H, dd, J=10 and 13 Hz, H-4), 3.05 (3H, m, Acetyl), 3.08 (1H, dd, J=3 and 13 Hz, H-3), 3.45 (4H, m, H-19, 25), 3.48 (3H, m, H-16, 22, 28), 3.54 (2H, d, J=6 Hz, H-12), 3.98 (1H, t, J=3 Hz, H-9), 3.99 (2H m, H-5), 4.06 (1H, dd, J=3 and 10 Hz, H-8), 4.14 (1H, t, J=6 Hz, H-11), 4.31 (1H, d, J=5 Hz, H-2), 4.58 (1H, d, J=4 Hz, H-10), 4.94 (1H, d, J=9 Hz, H-7).

(9) Investigation of ST-D Resistance Profiles in *E. coli* and *S. cerevisiae* Strains Overexpressing sttH or Nat Gene The following primers were designed and used in PCR for purposes of preparing an *E. coli* strain overexpressing the nat gene:

```
                                    (SEQ ID NO: 19)
5'-GGGGGATCCACCACTCTTGACGACACGGCT-3' (forward)

                                    (SEQ ID NO: 20)
5'-ACCAAGCTT TCAGGGGCAGGGCATGCTCAT-3' (reverse).
```

Restriction enzyme sites (GGATCC or AAGCTT, underlined) and a stop codon (TCA, underlined) were inserted into these primers. An expression vector (pQE30-nat) having incorporated therein an amplified fragment including these primers was constructed using pQE30. The MIC of ST-F and ST-D in an *E. coli* XL1-Blue MRF' strain carrying pQE30-nat and pQE30-SHF6R were determined on LB agar flat plates containing ampicillin (100 μg/mL), 0.1 mM IPTG and STs (0 to 4 mM). *S. cerevisiae* CKY8 strain overexpressing the nat gene and the sttH gene was also prepared as follows. The following two sets of primers having restriction enzyme sites (AAGCTT or CTGCAG, underlined) and stop codons (TCA, underlined) added thereto were designed and used in PCR:

```
                                    (SEQ ID NO: 21)
5'-ACCAAGCTTAATATGACCACTCTTGACGACACG-3'
(nat gene forward primer)

                                    (SEQ ID NO: 22)
5'-AAACTGCAG TCAGGGGCAGGGCATGCTCAT-3'
(nat gene reverse primer)

                                    (SEQ ID NO: 23)
5'-ACCAAGCTTACCATGCCCCCCGAGACCGCCGCG-3'
(sttH gene forward primer)

                                    (SEQ ID NO: 24)
5'-AAACTGCAG TCAGCGCGCTGGAGCGGGCGG-3'
(sttH gene reverse primer).
```

After sequence confirmation, the amplified fragments were inserted into the same sites in pAD4 to prepare pAD4-nat and pAD4-sttH, in which these genes were expressed under the control of the constitutive promoter of yeast alcohol dehydrogenase. *S. cerevisiae* CKY8 strain carrying pAD4-nat and pAD4-sttH was grown in SC-Leu medium containing ST (ST-F or ST-D, 0 to 4 mM), and the MICs of ST-F and ST-D were determined.

Example 1

Cloning and Nucleotide Sequencing of Streptothricin (ST) Resistance Gene

Interestingly, it was shown from minimum inhibitory concentration (MIC) testing of STs in *Streptomyces* strains believed to be ST non-producers that *Streptomyces albulus* NBRC14147 is more ST resistant than the ST producer *S. lavendulae* NBRC12789 (Table 1). Furthermore, using genomic DNA of NBRC14147 as the template no amplified fragment was obtained by PCR with primers designed for genes such as the nat gene coding for N-acetyltransferase (NAT) that acts on STs. On the other hand, a specific amplified fragment was detected using genomic DNA of *S. lavendulae* NBRC12789 as the template. Because the NBRC14147 strain was thus thought to have no homologous gene encoding NAT, this strain was selected for isolation of the ST resistance gene. Using an NBRC14147 genomic library constructed with the pWHM3 plasmid carrying a thiostrepton resistance gene, together with the *Streptomyces lividans* TK23 strain as a heterologous host exhibiting ST and thiostrepton sensitivity, many transformants of the TK23 strain exhibiting resistance to both thiostrepton (20 μg/mL) and STs (>400 μg/mL, mixture of ST-F and ST-D) were isolated. From these transformants, one transformant carrying a pWHM3 plasmid having a 2.9 kb fragment (pWHM3-st11, FIG. 2 and Table 1) was selected for further experiments because Southern blotting with the 2.9 kb fragment as a probe revealed that all of the plasmids isolated from these transformants had this 2.9 kb fragment.

Sequencing analysis of the 2.9 kb DNA fragment and codon frame analysis of *Streptomyces* strains (Bibb, M. J., Findlay, P. R. & Johnson, M. W., *Gene,* 30, 157-166 (1984)) showed two ORFs (ORF1 and ORF2) and one partial ORF (ORF3) (FIG. 2). To elucidate the functions of the individual ORFs, we used BLAST (Altschul, S. F. et al., *J. Mol. Biol.,* 215, 403-410 (1990)) and 3D-PSSM (Kelley, L. A., MacCallum, R. M. & Sternberg, M. J., *J. Mol. Biol,* 299, 499-520 (2000)) to search the databases (UniPro) with their translated products. The results are summarized in FIG. 2. In brief, the ORFs were similar to esterase and β-lactamase (ORF1), isochorismatase and other hydrolases (ORF2) and lipase (ORF3). Thus, no gene showing homology to the nat gene was found in this fragment. To verify which genes were responsible for the ST resistance, plasmids pWHM3-orf1 and pWHM3-orf2-3 were constructed carrying ORF1 and ORF2 to 3, respectively (FIG. 2), and introduced into *S. lividans* TK23. MIC testing confirmed that the transformant harboring pWHM3-orf2-3 exhibited ST resistance (Table 1). Considering that the pWHM3-orf2-3 plasmid carried the partial form of ORF3, this showed that it was ORF2 that conferred ST resistance. In this study, ORF2 showing similarity to hydrolase genes was designated sttH.

TABLE 1

Streptothricin (ST) Resistance Profile of Streptomyces Strains

| Streptomyces Strain | MIC (μg/mL) of ST | ST Production |
|---|---|---|
| *S. lavendulae* NBRC12789 | 400* | Yes |
| *S. albulus* NBRC14147 | >400* | No |
| *S. lividans* TK23 | 6.25* | No |
| + pWHM3 | 6.25[554] | — |
| + pWHM3-st1 1 | >400† | — |
| + pWHM3-orf2-3 | >400† | — |
| + pWHM3-orf1 | 6.25† | — |

Notes:

*5 plates of ATCC plate medium containing ST (0 to 400 μg/mL)

†5 plates of ATCC plate medium containing ST (0 to 400 μg/mL) and thiostrepton (20 μg/mL).

MIC determined after 3 days of culture at 30° C.

Example 2

Estimation of Start Codon of sttH Gene

On the basis of the results from the sequencing analysis and frame analysis, eight possible start codons (ATG and GTG, positions 1 to 8 shown in FIG. 2) were found in the sttH gene. It was also difficult to predict the start codon from the nucleotide sequence information because no apparent and characteristic nucleotide sequences for a set of promoter region and ribosome binding site are known in general for *Streptomyces* strains. Six kinds of SttH recombinant enzymes (sometimes abbreviated here as "rSttH") each having a different N-terminal region were therefore prepared as N-terminal 6× His Tag fused proteins, and a start codon was estimated based on their enzymatic activities, which were evaluated based on MIC values. Expression plasmids for *E. coli*, pQE30-SHF1R (carrying the sttH gene from position 1), pQE30-SHF2R (position 2), pQE30-SHF3R (position 3 and 4), pQE30-SHF4R (position 5), pQE30-SHF5R (position 6 and 7) and pQE30-SHF6R (position 8) were constructed. pQE30-SHF7R was also constructed even though the GTG codon of position 9 was expected not to be a possible start codon due to the extremely short peptide length of the translation product. After introduction of these 7 plasmids and pQE30 (no insert) into *E. coli*, the MICs of STs were determined to be 12.5 μg/mL (the *E. coli* strain having pQE30), 50 μg/mL (pQE30-SHF1R), 50 μg/mL (pQE30-SHF2R), 50 μg/mL (pQE30-SHF3R), 100 μg/mL (pQE30-SHF4R), 100 μg/mL (pQE30-SHF5R), >100 μg/mL (pQE30-SHF6R), and 12.5 μg/mL (pQE30-SHF7R), suggesting that the position 8 codon could operate as a start codon in *S. albulus* NBRC14147.

Example 3

Figure 3:
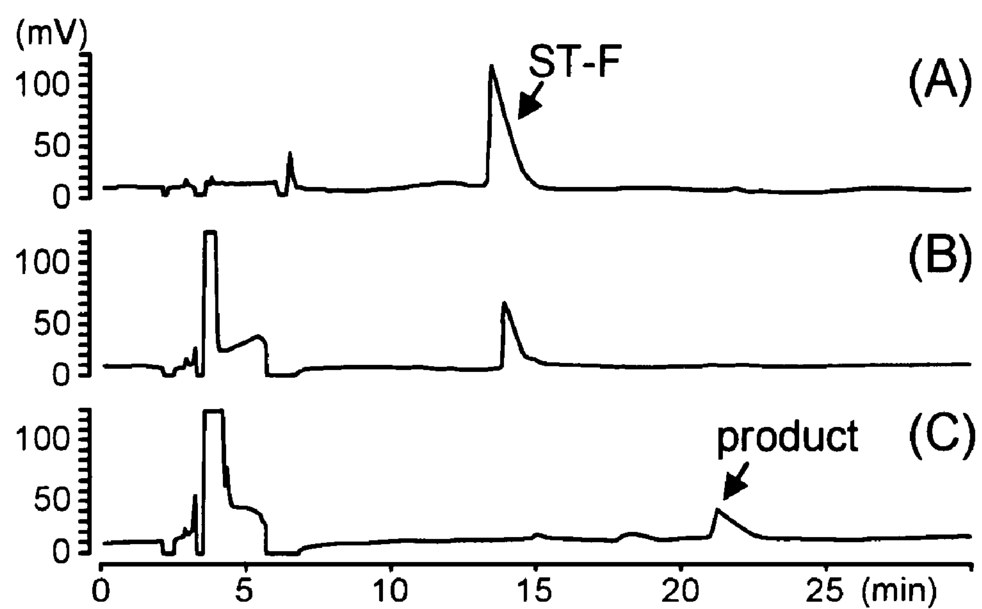
FIG. 3 illustrates the results of HPLC analysis of substances produced by rSttH. ST-F reacted with rSttH (C), ST-F without rSttH added (B) and reaction liquid and ST-F standard substance (A) were analyzed by reverse-phase HPLC. The HPLC conditions were as described under "Materials and Methods.

Identification and Structural Determination of ST-F and ST-D Derived Compounds Converted by rSttH rSttH that had been highly purified by Ni-affinity chromatography was incubated with ST-F. An rSttH-dependent product which was eluted with a retention time longer than that of ST-F in reverse-phase HPLC was specifically detected in the reaction mixture, which contained no additives such as cofactors or metal ions (FIG. 3C). Likewise, an rSttH-dependent product was also detected when ST-D was used as the substrate. To determine the structures of the rSttH-dependent products thus obtained, these compounds were purified and analyzed by positive ion electrospray ionization mass spectrometry (ESI-MS) and NMR. The ESI-MS data showed that the ST-F derived compound had a molecular weight of 521, 18 daltons greater than the molecular weight (503 Da) of ST-F (FIG. 4), and the tandem mass (ESI-MS/MS) data showed that this change occurred in the streptolidine lactam moiety. A similar pattern was also seen in the case of the ST-D derived compound. These results strongly suggest that rSttH catalyzed the hydrolysis of the amide bond of streptolidine lactam. NMR analysis was performed to confirm these predicted structures, and the resulting $^1$H NMR spectral features of the streptolidine lactam moiety (see "Materials and Methods") were in complete agreement with those of a chemically synthesized streptolidine that was reported by Zabriskie et al (Jackson, M. D., Gould, S. J. & Zabriskie, T. M., J. *Org. Chem.,* 67, 2934-2941 (2002)). The ST-F and ST-D derived products produced by the action of rSttH were thus determined to be ST-F-acid (compound of Formula (I) above in which n=1) and ST-D-acid (compound of Formula (I) above in which n=3), respectively.

Example 4

Enzymatic Properties of rSttH

The optimal pH was measured in several buffers (100 mM) with differing pH values: sodium phosphate (NaPB), pH 4.5 to 7; Tris-HCl, pH 7 to 10. Activity peaked at a pH of 6.5 and declined rapidly with decreasing pH (around 4). The effect of temperature on enzymatic activity was also investigated within the range of 25° C. to 75° C. using 100 mM NaPB buffer (pH 6.5). Although enzymatic activity was greatest at 45° C., approximately 90% of maximum activity was also detected at 65° C. The kinetic parameters are summarized in Table 2. The $K_m$ values of the rSttH were calculated to be 0.96±0.19 mM for ST-F and 5.74±0.99 mM for ST-D, showing that the enzyme has higher affinity for the ST compound having a shorter β-lysine polymer chain. However, the $V_{max}$ value of rSttH for ST-D was slightly higher than that for ST-F. The calculated $V_{max}/K_m$ value of the reaction with ST-F was 4-fold higher than that of the reaction with ST-D. The native molecular mass of rSttH ORF2 was estimated to be 50 kDa by gel filtration, suggesting that rSttH exists as a homodimer.

TABLE 2

Kinetic Parameters* of Streptothricin (ST)

| Substrate | $K_m$ (mM) | $V_{max}$ (U†/mg) | $V_{max}/K_m$ (U†/mg/mM) |
|---|---|---|---|
| ST-F | 0.96 ± 0.19 | 42.26 ± 2.8 | 44.01 |
| ST-D | 5.74 ± 0.99 | 68.95 ± 13.9 | 11.99 |

Notes:

*Kinetic parameters determined at 30° C. using 100 mM NaPB (pH 6.5)

†U, ST-acid production per minute (μmol). Each calculated value is the average + s.d. from three tests Example 5

Investigation of ST-D Resistance Profile in *E. coli* and Yeast Cells Overexpressing sttH or Nat Gene and in Other Microorganisms Although it was previously reported that the biological activity of chemically synthesized ST-F-acid is negligible in microorganisms and plants, that of ST-D-acid remains unclear. Therefore, we determined the respective MICs of ST-F and ST-D in *E. coli* and *Saccharomyces cerevisiae* overexpressing the sttH gene or nat gene (Table 3). The strains of *E. coli* (pQE-nat) and *S. cerevisiae* (pAD4-nat) having the nat gene exhibited resistance to both ST-F and ST-D as reported previously. Interestingly, however, the MIC value of ST-D was found to be extremely low in *E. coli* overexpressing rSttH (pQE30-SHF6R) in contrast to the results for *S. cerevisiae* overexpressing rSttH (pAD4-sttH), indicating that ST-D-acid was still active as an antibacterial agent against prokaryotic cells. To confirm this, the selective toxicity of ST-acids and STs against various microorganisms including gram-positive and -negative bacteria, clinically isolated pathogenic bacteria and yeasts was investigated. The MIC studies revealed that in contrast to the ST-F-acid, which had lost almost all of its antimicrobial activity with respect to both prokaryotic and eukaryotic cells, the ST-D-acid exhibited no activity with respect to eukaryotic cells such as *S. cerevisiae* and *Schizosaccharomyces pombe* but actually exhibited a high level of activity with respect to bacteria such as *E. coli, Bacillus subtilis* and *Staphylococcus aureus* (Table 3). A “c/a” in parentheses in the table represents the ratio of the minimum inhibitory concentrations of ST-F-acid and ST-F, while “d/b” represents the ratio of the minimum inhibitory concentrations of ST-D-acid and ST-D.

TABLE 3

Minimum Inhibitory Concentrations (MICs) of ST Compounds in Prokaryotic and Eukaryotic Cells

| Strain | Minimum inhibitory concentration (MIC) (mM) | | | |
|---|---|---|---|---|
| | ST-F[a] | ST-D[b] | ST-F-acid[c] (c/a)[¶] | ST-D-acid[d] (d/b)[¶] |
| *S. cerevisiae* CKY8* | | | | |
| + pAD4 | 0.5 | <0.03 | NT | NT |
| + pAD4-nat | >4 | >4 | NT | NT |
| + pAD4-sttH | >4 | >4 | NT | NT |
| *E. coli* XL1-Blue MRF'† | | | | |
| + pQE30 | <0.03 | <0.03 | NT | NT |
| + pQE30-nat | 4 | 2 | NT | NT |
| + pQE30-SHF6R | 0.25 | <0.03 | NT | NT |
| *S. cerevisiae* S288C‡ | 0.062 | 0.004 | >4 (>64) | 1 (250) |
| *S. pombe* L972‡ | 0.125 | 0.008 | >4 (>32) | 1 (125) |
| *E. coli* W3110§ | 0.03 | 0.008 | 4 (133) | 0.25 (31.3) |
| *B. subtilis* NBRC13169§ | 0.016 | 0.004 | 4 (250) | 0.125 (31.3) |
| *S. aureus* AB§ | 0.016 | 0.004 | 2 (126) | 0.06 (15) |
| *S. aureus* FIR1169§ | 0.016 | 0.004 | 2 (126) | 0.06 (15) |

Notes:
*Microorganism cultured in SC medium.
†Microorganism cultured in LB medium.
‡Microorganism cultured in YPD medium.
§Microorganism cultured in Heart Infusion Broth (Difco) medium.
Yeasts grown for 2 days at 30° C., bacteria for 1 day at 37° C.
rcentage of inactivated ST-acid. NT = not studied.

Due to the opening of the lactam ring of streptothricin, the protein of the invention can reduce the antibiotic activity (that is, toxicity) of streptothricin with respect to eukaryotic cells without sacrificing antibiotic activity with respect to prokaryotic cells, it is useful in the manufacture of streptothricin derivatives that have potential for clinical development and as lead compounds for drug discovery.

Moreover, because the polynucleotide of the invention can confer streptothricin resistance on eukaryotic cells (such as yeasts), it is useful as an antibiotic resistance marker gene for use in recombinant DNA technology. The ST and nat genes are currently used in recombinant DNA technology in prokaryotic and eukaryotic cells, and these could be replaced by a combination of ST-D (which has more antibiotic activity than ST-F) and the sttH gene in eukaryotic cells, particularly yeasts.

Additionally, because ST-D-acid has reduced antibiotic activity (that is, toxicity) with respect to eukaryotic cells while retaining antibiotic activity with respect to prokaryotic cells, it is useful as an antimicrobial agent with potential for clinical development, and as a lead compound in the discovery of such antimicrobial agents. That is, as shown in Table 3, approximately 4 to approximately 17 times more of the physiological activity of ST-D-acid was inactivated in yeasts than in bacteria. ST-D-acid was found to have particularly strong antimicrobial activity with respect to the clinically isolated pathogenic bacteria *S. aureus* AB (unreported enterotoxin AB-producing strain) and *S. aureus* FIR 1169 (toxic shock syndrome exotoxin-producing strain) (Igarashi, H. et al., *Infect. Immun.,* 44, 175-181 (1984)). ST is a strong antibiotic against various bacteria, but has not been clinically developed because it is toxic in mammals. However, in the invention ST-D-acid has reduced toxicity with respect to eukaryotic cells while retaining strong antimicrobial activity, showing that ST-D-acid could be clinically developed or used as a novel lead compound for drug discovery.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention

What is claimed is:

1. A method for manufacturing a lactam ring-opened streptothricin derivative or salt thereof, comprising a step of:

contacting a protein with a substance containing a lactam ring to open the lactam ring, wherein said protein is encoded for by the polynucleotide comprising at least one of (a) through (d) below:

(a) a polynucleotide containing a polynucleotide comprising a nucleotide sequence selected from the group consisting of SEQ ID NO: 1, 3, 5, 7, 9, 11, 13 and 15;

(b) a polynucleotide containing a polynucleotide encoding for a protein comprising an amino acid sequence selected from the group consisting of SEQ ID NO: 2, 4, 6, 8, 10, 12, 14 and 16;

(c) a polynucleotide containing a polynucleotide encoding for a protein comprising an amino acid sequence selected from the group consisting of SEQ ID NO: 2, 4, 6, 8, 10, 12, 14 and 16 with 1-10 of amino acids deleted, substituted, inserted and/or added and having lactam ring-opening activity; and (d) a polynucleotide containing a polynucleotide encoding for a protein having an amino acid sequence that has 90% or more identify with an amino acid sequence selected from the group consisting of SEQ ID NO: 2, 4, 6, 8, 10, 12, 14 and 16, and having lactam ring-opening activity.

2. The manufacturing method according to claim 1, wherein the polynucleotide is any of (e) through (f) below:

(e) a polynucleotide containing a polynucleotide encoding for a protein comprising an amino acid sequence selected from the group consisting of SEQ ID NO: 2, 4, 6, 8, 10, 12, 14 and 16 with 1-6 of amino acids deleted, substituted, inserted and/or added and having lactam ring-opening activity; and (f) a polynucleotide containing a polynucleotide encoding for a protein having an amino acid sequence having 95% or more identity with an amino acid sequence selected from the group consisting of SEQ ID NO 2, 4, 6, 8, 10, 12, 14 and 16, and having lactam ring-opening activity.

3. The manufacturing method according to claim 1, wherein the polynucleotide is any of (g) through (h) below:

(g) a polynucleotide containing a polynucleotide encoding for a protein comprising an amino acid sequence selected from the group consisting of SEQ ID NO 2, 4, 6, 8, 10, 12, 14 and 16 with 1-3 of amino acids deleted, substituted, inserted and/or added and having lactam ring-opening activity; and (h) a polynucleotide containing a polynucleotide encoding for a protein having an amino acid sequence that has 98% or more identify with an amino acid sequence selected from the group consisting of SEQ ID NO: 2, 4, 6, 8, 10, 12, 14 and 16, and having lactam ring-opening activity.

4. The manufacturing method according to claim 1, wherein the polynucleotide comprises a polynucleotide comprising the nucleotide sequence of SEQ ID NO: 1.

5. The manufacturing method according to claim 1, wherein the polynucleotide comprises a polynucleotide encoding for a protein comprising the amino acid sequence of SEQ ID NO: 2.

6. The manufacturing method according to claim 1, wherein the polynucleotide is DNA.

7. The manufacturing method according to claim 1, wherein the protein comprising an amino acid sequence selected from the group consisting of SEQ ID NO: 2, 4, 6, 8, 10, 12, 14 and 16.

8. The manufacturing method according to claim 1, wherein the protein comprises an amino acid sequence of SEQ ID NO: 2.

9. The manufacturing method according to claim 1, wherein the lactam ring-opened streptothricin derivative is a compound represented by Formula (I):

(I)

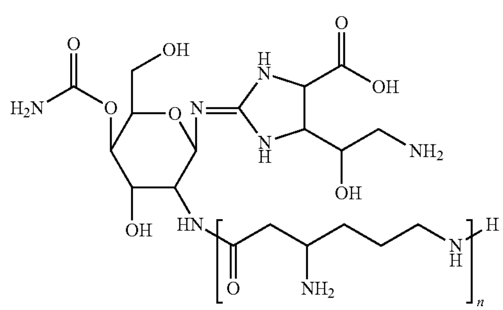

(wherein n is an integer between 1 and 7).

10. The manufacturing method according to claim 2, wherein the lactam ring-opened streptothricin derivative is a compound represented by Formula (I):

(I)

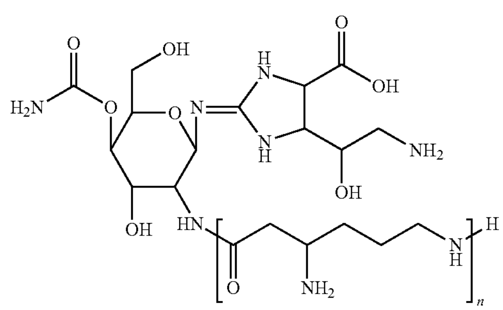

(wherein n is an integer between 1 and 7).

11. The manufacturing method according to claim 3, wherein the lactam ring-opened streptothricin derivative is a compound represented by Formula (I):

(I)

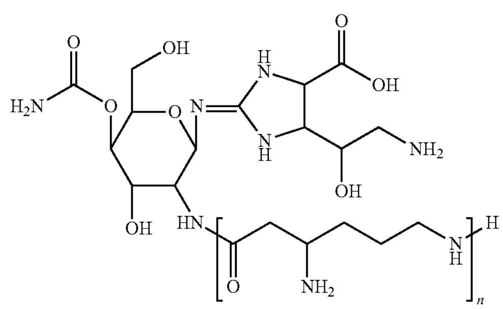

(wherein n is an integer between 1 and 7).

12. The manufacturing method according to claim 4, wherein the lactam ring-opened streptothricin derivative is a compound represented by Formula (I):

(I)

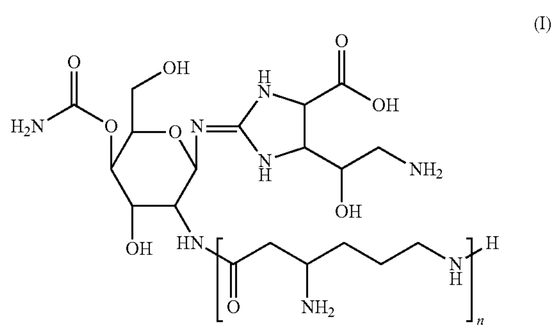

(wherein n is an integer between 1 and 7).

13. The manufacturing method according to claim 7, wherein the lactam ring-opened streptothricin derivative is a compound represented by Formula (I):

(I)

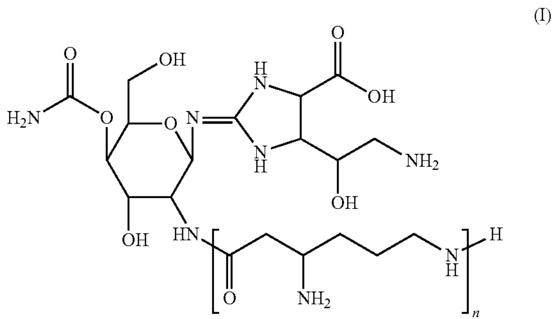

(wherein n is an integer between 1 and 7).

14. The manufacturing method according to claim 9, wherein the compound represented by Formula (I) is a compound represented by Formula (II):

(II)

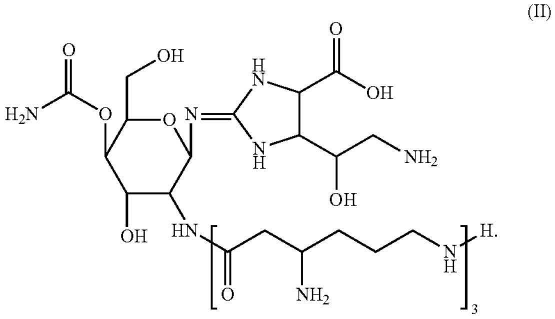

15. The manufacturing method according to claim 10, wherein the compound represented by Formula (I) is a compound represented by Formula (II):

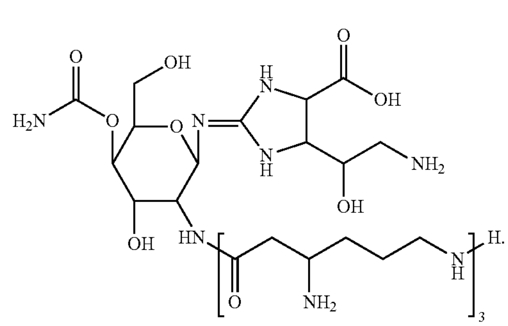

16. The manufacturing method according to claim 11, wherein the compound represented by Formula (I) is a compound represented by Formula (II):

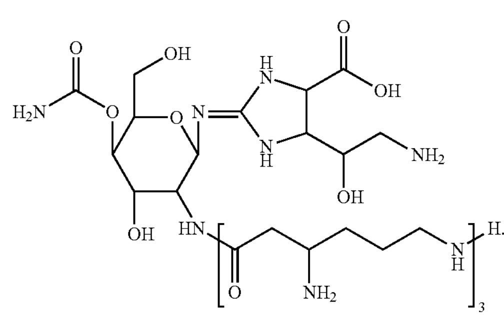

17. The manufacturing method according to claim 12, wherein the compound represented by Formula (I) is a compound represented by Formula (II):

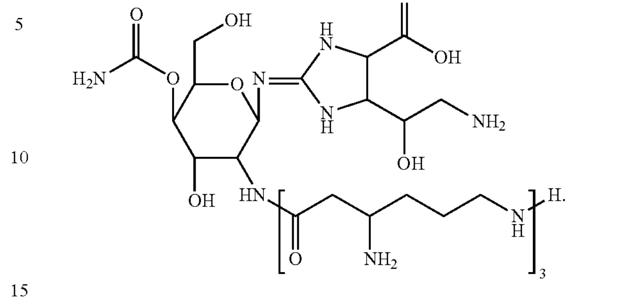

18. The manufacturing method according to claim 13, wherein the compound represented by Formula (I) is a compound represented by Formula (II):

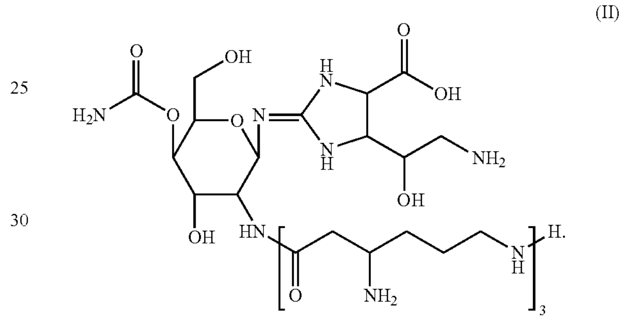

* * * * *